US011882366B2

(12) United States Patent
Soreefan et al.

(10) Patent No.: US 11,882,366 B2
(45) Date of Patent: Jan. 23, 2024

(54) PATIENT MONITORING SYSTEM

(71) Applicant: Hill-Rom Services, Inc., Batesville, IN (US)

(72) Inventors: Ibne Soreefan, West Chester, OH (US); Tyler Holmes, Monroe, CT (US); Eric Dustin Agdeppa, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/679,381

(22) Filed: Feb. 24, 2022

(65) Prior Publication Data

US 2022/0321756 A1 Oct. 6, 2022

Related U.S. Application Data

(60) Provisional application No. 63/154,300, filed on Feb. 26, 2021.

(51) Int. Cl.
*G06V 10/00* (2022.01)
*H04N 23/72* (2023.01)
(Continued)

(52) U.S. Cl.
CPC ............ *H04N 23/72* (2023.01); *A61B 5/0077* (2013.01); *A61B 5/015* (2013.01); *A61B 5/7278* (2013.01);
(Continued)

(58) Field of Classification Search
CPC ........ H04N 23/72; H04N 23/56; H04N 23/90; A61B 5/0077; A61B 5/015; A61B 5/7278;
(Continued)

(56) References Cited

U.S. PATENT DOCUMENTS 6,061,088 A * 5/2000 Khosravi ............... G06V 10/28
348/700
6,570,608 B1 * 5/2003 Tserng .................... G06V 40/20
348/700
(Continued)

FOREIGN PATENT DOCUMENTS

CN 104434033 A 3/2015
CN 109948433 A 6/2019
(Continued)

OTHER PUBLICATIONS

Hu, et al., "Combination of Near-Infrared and Thermal Imaging Techniques for the Remote and Simultaneous Measurements of Breathing and Heart Rates Under Sleep Situation" Plos One, Jan. 5, 2018, pp. 1-14.
(Continued)

*Primary Examiner* — Frank F Huang
(74) *Attorney, Agent, or Firm* — Price Heneveld LLP

(57) ABSTRACT

A patient monitoring system includes a first imager configured to capture first image data of a target area within a first field of view. A second imager is configured to capture second image data of the target area within a second field of view. An emitter is configured to emit light within a predetermined wavelength range. A controller is configured to determine a facial region of a person in the first image data, determine a region of interest in the second image data that coincides with the facial region in the first image data, calculate a pixel value within the region of interest, adjust at least one of the emitter and the second imager is the pixel value is outside a predetermined pixel value range, and determine vital signs information from at least one of the first image data and the second image data.

20 Claims, 20 Drawing Sheets

(51) Int. Cl.
*A61B 5/00* (2006.01)
*A61B 5/01* (2006.01)
*H04N 23/56* (2023.01)
*H04N 23/90* (2023.01)
*G06V 10/25* (2022.01)
*G06V 20/52* (2022.01)
*G06V 40/16* (2022.01)

(52) U.S. Cl.
CPC ........... *A61B 5/7485* (2013.01); *H04N 23/56* (2023.01); *H04N 23/90* (2023.01); *A61B 2576/02* (2013.01); *G06V 10/25* (2022.01); *G06V 20/52* (2022.01); *G06V 40/161* (2022.01)

(58) Field of Classification Search
CPC .. A61B 5/7485; A61B 2576/02; G06V 10/25; G06V 20/52; G06V 40/161; G16H 30/20
See application file for complete search history.

(56) References Cited

U.S. PATENT DOCUMENTS

| | | | |
|---|---|---|---|
| 6,633,232 B2* | 10/2003 | Trajkovic | G06Q 30/06 348/143 |
| 7,987,069 B2 | 7/2011 | Rodgers et al. | |
| 8,149,273 B2 | 4/2012 | Liu et al. | |
| 8,542,872 B2* | 9/2013 | Gornick | G06T 17/05 382/106 |
| 8,571,261 B2* | 10/2013 | Gagvani | G06V 20/49 340/541 |
| 9,301,689 B2 | 4/2016 | Vanderpohl | |
| 9,560,974 B2 | 2/2017 | Tolosa et al. | |
| 9,750,420 B1 | 9/2017 | Agrawal et al. | |
| 9,928,607 B2 | 3/2018 | Jeanne et al. | |
| 9,962,095 B2 | 5/2018 | Ahmad et al. | |
| 10,159,443 B2 | 12/2018 | Bresch et al. | |
| 10,258,242 B2 | 4/2019 | Godavaarty et al. | |
| 10,806,356 B2 | 10/2020 | Lee et al. | |
| 10,904,492 B2 | 1/2021 | Derenne et al. | |
| 2004/0100563 A1* | 5/2004 | Sablak | H04N 23/611 348/E7.087 |
| 2005/0286741 A1* | 12/2005 | Watanabe | H04N 19/63 375/E7.134 |
| 2009/0066790 A1* | 3/2009 | Hammadou | G08B 13/19663 348/E5.062 |
| 2009/0161981 A1* | 6/2009 | Allen | G06T 7/215 382/103 |
| 2009/0310862 A1* | 12/2009 | Tu | G06V 20/53 382/173 |
| 2010/0290710 A1* | 11/2010 | Gagvani | G06T 7/194 382/224 |
| 2010/0316257 A1* | 12/2010 | Xu | G06V 10/255 382/103 |
| 2011/0102627 A1* | 5/2011 | Okada | H04N 21/4728 348/222.1 |
| 2011/0134245 A1* | 6/2011 | Khizhnichenko | G06V 20/52 348/148 |
| 2012/0078088 A1 | 3/2012 | Whitestone et al. | |
| 2012/0081552 A1* | 4/2012 | Sablak | H04N 23/61 348/169 |
| 2012/0283530 A1 | 11/2012 | Maynard et al. | |
| 2014/0085545 A1* | 3/2014 | Tu | G06F 18/254 348/E9.047 |
| 2014/0253709 A1 | 9/2014 | Bresch et al. | |
| 2014/0254670 A1* | 9/2014 | Kwon | H04N 19/157 375/240.12 |
| 2014/0275832 A1 | 9/2014 | Muehlsteff et al. | |
| 2015/0023552 A1 | 1/2015 | Rosen | |
| 2015/0178953 A1* | 6/2015 | Gao | G06T 11/00 345/681 |
| 2015/0294549 A1 | 10/2015 | Ribble | |
| 2015/0312575 A1* | 10/2015 | Bryant | H04N 19/167 375/240.08 |
| 2017/0220870 A1* | 8/2017 | Roth | G06V 20/52 |
| 2019/0000391 A1 | 1/2019 | De Haan et al. | |
| 2019/0075302 A1* | 3/2019 | Huang | H04N 19/52 |
| 2019/0108387 A1 | 4/2019 | Rivard et al. | |
| 2020/0105407 A1 | 4/2020 | Soreefan et al. | |
| 2020/0155040 A1 | 5/2020 | Soreefan et al. | |
| 2020/0178809 A1 | 6/2020 | Wang et al. | |
| 2020/0219604 A1 | 7/2020 | Hallack et al. | |
| 2020/0234439 A1 | 7/2020 | Chang et al. | |
| 2020/0297247 A1 | 9/2020 | Clark et al. | |
| 2020/0367762 A1 | 11/2020 | Wallace | |

FOREIGN PATENT DOCUMENTS

| | | |
|---|---|---|
| CN | 110060272 A | 7/2019 |
| EP | 2994880 B1 | 6/2017 |
| EP | 3207862 A1 | 8/2017 |
| KR | 101426750 B1 | 8/2014 |
| WO | 2017146643 A1 | 8/2017 |
| WO | 2020137276 A1 | 2/2020 |
| WO | 2020052626 A1 | 3/2020 |

OTHER PUBLICATIONS

Nam, et al., "Monitoring of Heart and Breathing Rates Using Dual Cameras on a Smartphone", Plos One 11(3), Mar. 10, 2016, pp. 1-15.

* cited by examiner

PATIENT MONITORING SYSTEM

CROSS-REFERENCE TO RELATED APPLICATION

This application claims priority to U.S. Provisional Patent Application No. 63/154,300, filed on Feb. 26, 2021, entitled "PATIENT MONITORING SYSTEM," the disclosure of which is hereby incorporated herein by reference in its entirety.

FIELD OF THE DISCLOSURE

The present disclosure generally relates to a monitoring system, and more particularly to a contactless patient monitoring system for a medical facility.

SUMMARY OF THE DISCLOSURE

According to one aspect of the present disclosure, a contactless patient monitoring system includes a first imager configured to capture first image data of a target area within a first field of view. A second imager is operably coupled to the first imager. The second imager is configured to capture second image data of the target area within a second field of view. An emitter is operably coupled to at least one of the first imager and the second imager. The emitter is configured to emit light within a predetermined wavelength range. A controller is communicatively coupled to the first imager, the second imager, and the emitter. The controller is configured to determine a facial region of a person in the first image data, determine a region of interest in the second image data that coincides with the facial region in the first image data, calculate a pixel value within the region of interest, adjust at least one of the emitter and the second imager when the pixel value is outside a predetermined pixel value range, and determine vital signs information from at least one of the first image data and the second image data.

According to another aspect of the present disclosure, a monitoring system for a medical facility includes a thermal imager configured to capture thermal image data. A monochromatic imager is configured to capture monochromatic image data. An emitter has a light source operably coupled to light control circuitry. A controller is communicatively coupled to the thermal imager, the monochromatic imager, and the emitter. The controller is configured to determine a thermal facial region within the thermal image data, map a region of interest onto the monochromatic image data that coincides with the thermal facial region, calculate a pixel value within the region of interest in the monochromatic image data, and adjust an intensity of light emitted by the light source in response to the pixel value.

According to another aspect of the present disclosure, a contactless patient monitoring system includes a first imager is configured to capture first image data. A second imager is configured to capture second image data. An emitter is disposed proximate to at least the second imager. The emitter is configured to emit light. A controller is configured to communicate with the first imager, the second imager, and the emitter. The controller is configured to determine a center point of a facial region utilizing a first image data received from the first imager, map a corresponding central point on a second image data received from the second imager that coincides with the center point of the facial region of the first image data, determine a region of interest on the second image data utilizing the central point, calculate a pixel value within the region of interest, compare the pixel value with a predetermined pixel value range, and adjust at least one of an exposure of the second imager and an intensity of light emitted by the emitter if the pixel value is outside of the predetermined pixel value range.

These and other features, advantages, and objects of the present disclosure will be further understood and appreciated by those skilled in the art by reference to the following specification, claims, and appended drawings.

DETAILED DESCRIPTION

Figure 1:
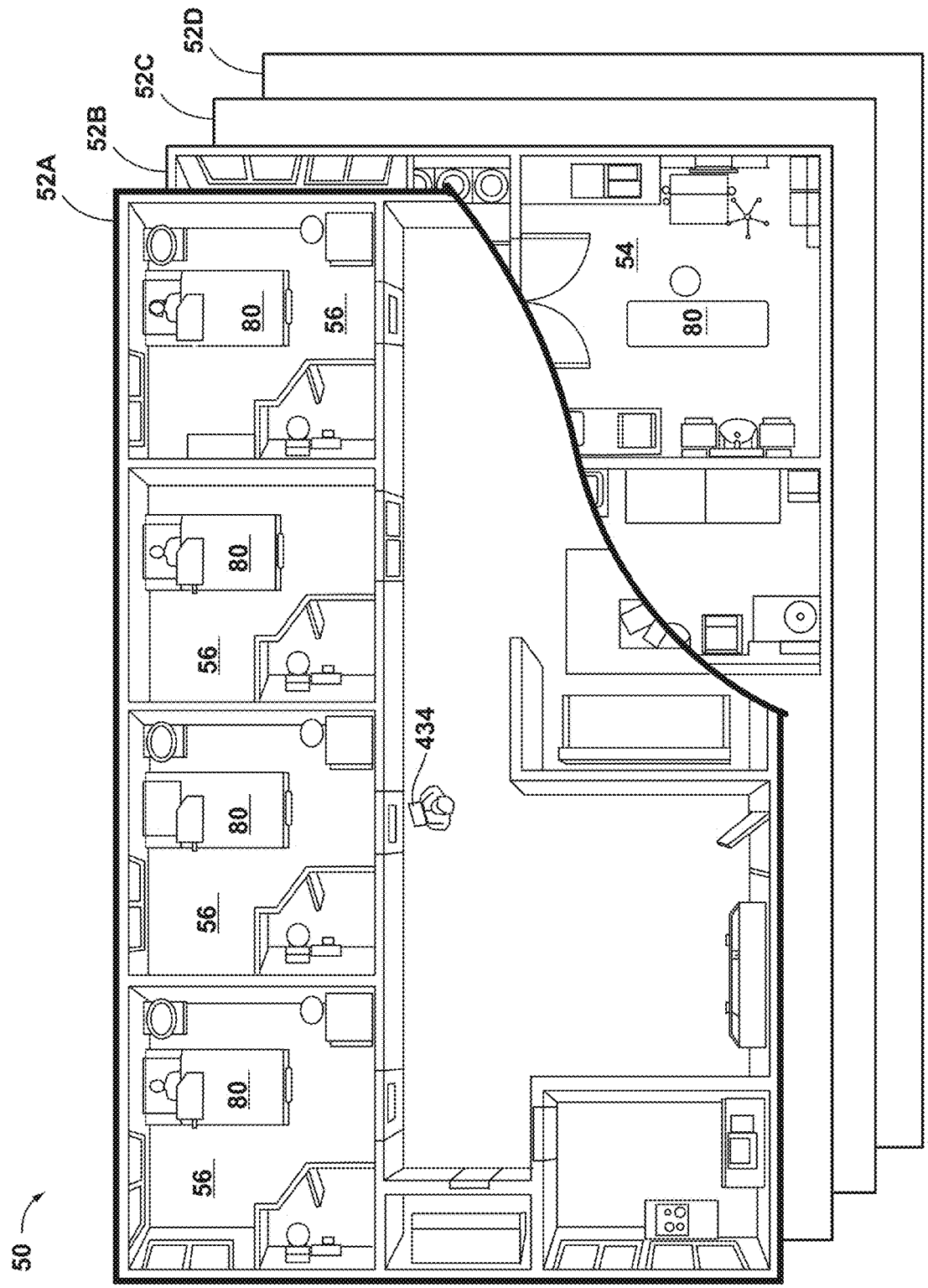
FIG. 1 is a schematic diagram of a portion of a medical facility, according to the present disclosure.

The present illustrated embodiments reside primarily in combinations of method steps and apparatus components related to a patient monitoring system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-25, reference numeral 10 generally designates a contactless patient monitoring system that includes a first imager 12 configured to capture first image data 14 of the target area 16 within a first field of view 18. A second imager 20 is operably coupled to the first imager 12 and is configured to capture second image data 22 of the target area 16 within a second field of view 24. An emitter 26 is operably coupled to at least one of the first imager 12 and the second imager 20. The emitter 26 is configured to emit light 28 within a predetermined wavelength range. A controller 30 is communicatively coupled to the first imager 12, the second imager 20, and the emitter 26. The controller 30 is configured to determine a facial region 32 of a person in the first image data 14. The controller 30 is also configured to determine a region of interest (ROI) 34 in the second image data 22 that coincides with the facial region 32 in the first image data 14. Additionally, the controller 30 is configured to calculate an average pixel value within the ROI 34.

Referring to FIG. 1, the monitoring system 10 provides a contactless method for monitoring a patient. A person may become a patient at a medical facility 50 for treatment, for a procedure, for monitoring, or for receiving other types of care. The patient may be transported between several areas or units while at the medical facility 50. For example, the patient may be transferred between different departments on different floors 52A-52D within the medical facility 50 depending on the treatment or procedure to be received. For example, the patient may be transported between a surgical suite 54 for one or more surgical procedures and a patient room 56 for recovery. Depending on the care to be received by the patient, the patient may stay at the medical facility 50 for a period of time. In such circumstances, the patient may stay in the patient room 56 for monitoring and care.

Figure 2:
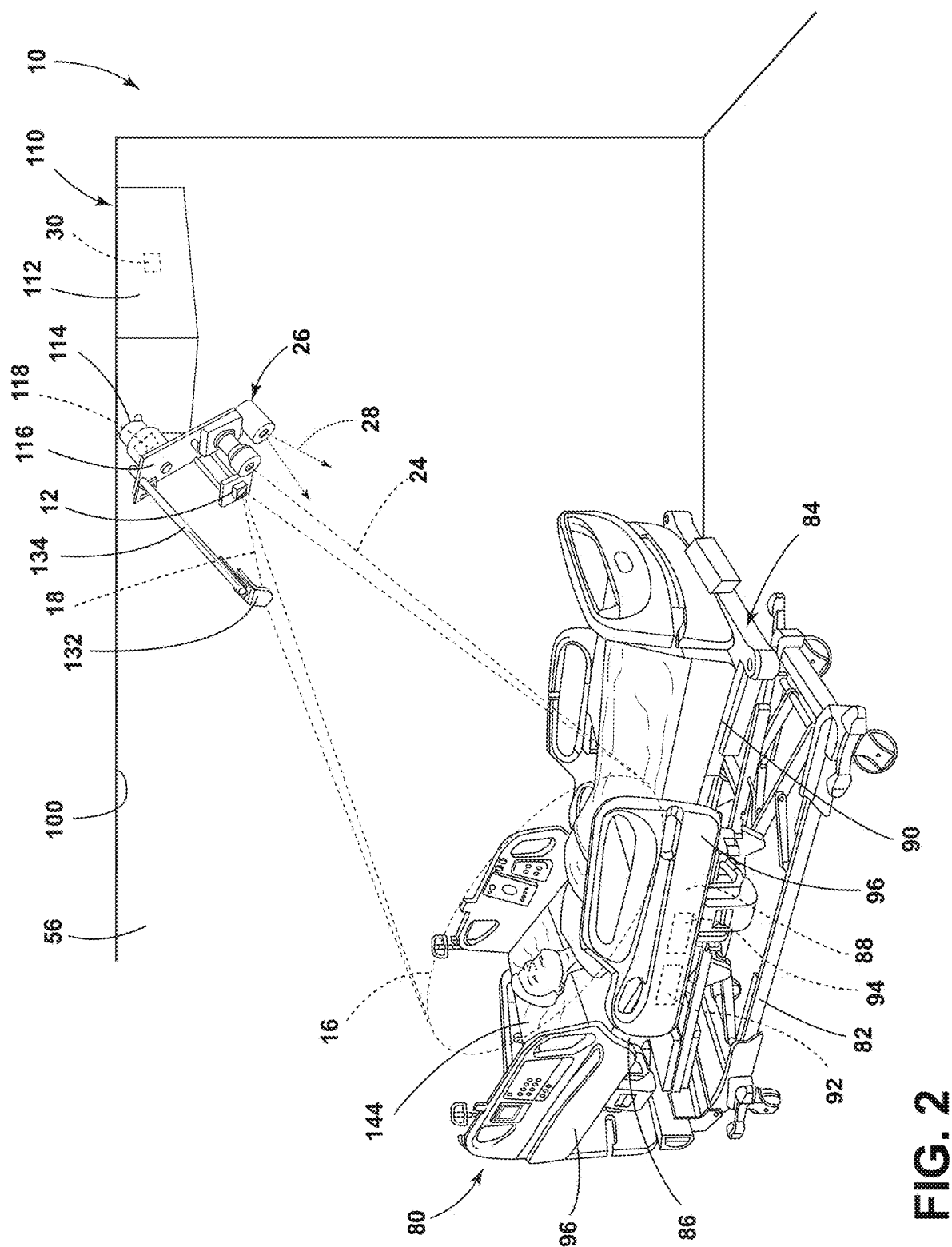
FIG. 2 is a side perspective view of a patient room having a monitoring system, according to the present disclosure.
Figure 3:
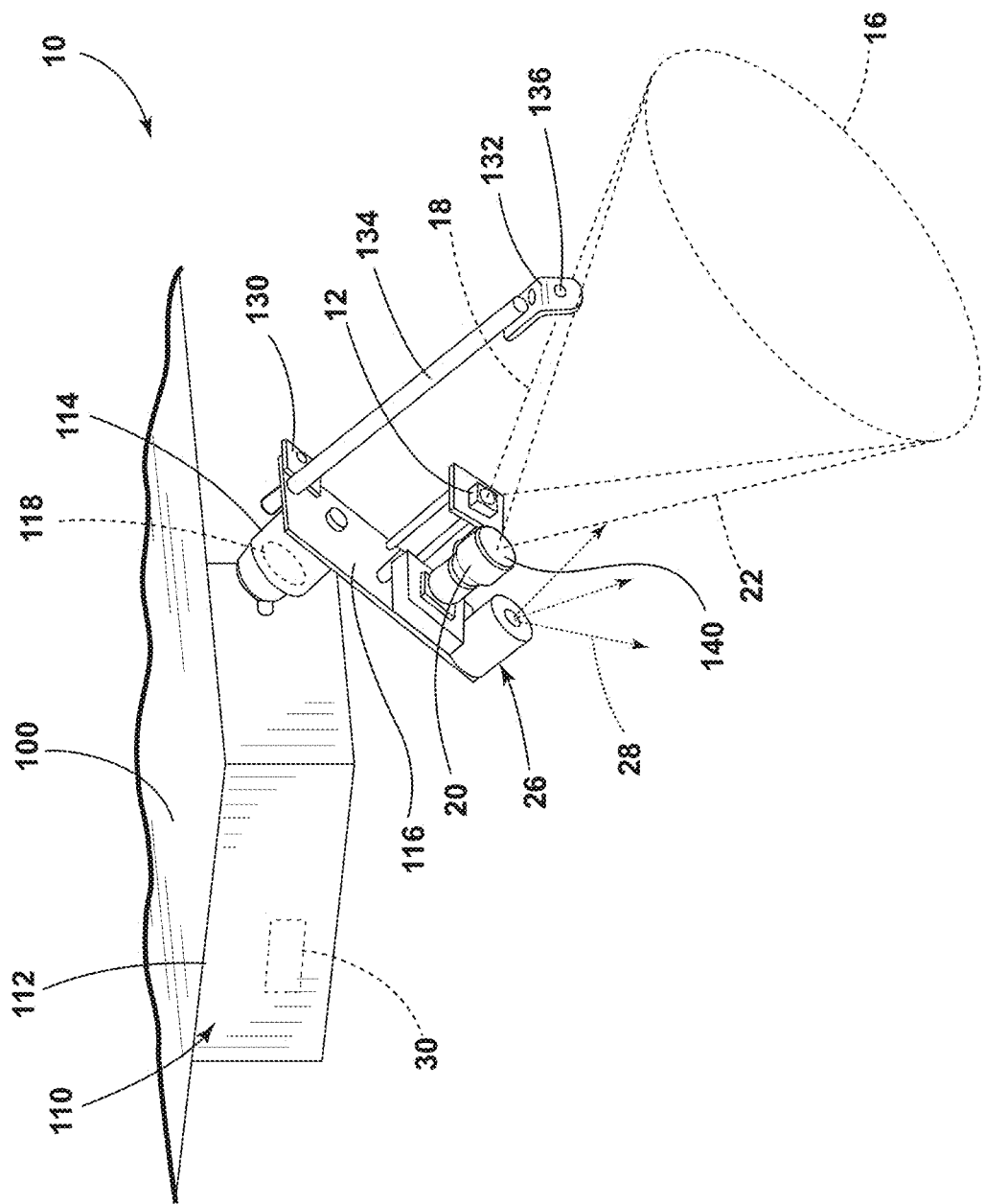
FIG. 3 is a side perspective view of a monitor assembly, according to the present disclosure.

Referring to FIGS. 2 and 3, during the stay at the medical facility 50, caregivers generally monitor the patient, which includes monitoring vital signs information 70. The vital signs information 70 may be monitored utilizing the monitoring system 10, which generally provides a contactless and continuous method for monitoring the patient. In the example illustrated in FIG. 2, the monitoring system 10 is included in the patient room 56. However, it is contemplated that each room including, for example, patient rooms 56, surgical suites 54, imaging rooms, etc., may utilize the monitoring system 10 to obtain and monitor health information about the patient.

In the illustrated example of the patient room 56 of FIG. 2, the patient is positioned on a support apparatus 80. The support apparatus 80 is illustrated as a medical bed, but may also be configured as a surgical table, a stretcher, or other structure for supporting the patient. The support apparatus 80 generally includes a base frame 82 and an upper frame 84 coupled to the base frame 82. The upper frame 84 is adjustable relative to the base frame 82 (e.g. raise, lower, tilt, etc.). Additionally, in the illustrated example, the upper frame 84 includes multiple segments 86, 88, 90 that are independently adjustable relative to one another, allowing the upper frame 84 to articulate between various positions (e.g., an elevated head region, an elevated foot region, etc.).

The support apparatus 80 generally includes actuation assemblies 92, 94 configured to adjust the position of the upper frame 84. One actuation assembly 92 may adjust the upper frame 84 relative to the base frame 82, while the other actuation assembly 94 may adjust the independent segments 86, 88, 90 of the upper frame 84 relative to one another. The support apparatus 80 also includes siderails 96, which may be raised and lowered to selectively prevent or allow ingress and egress on the support apparatus 80. The siderails 96 may be manually adjusted or may be automatically adjusted. Information relating to a position of the support apparatus 80 and a position of the patient on the support apparatus 80 may be utilized by the monitoring system 10 as described herein.

Referring still to FIGS. 2 and 3, the monitoring system 10 is generally utilized for determining a variety of information about the patient on the support apparatus 80 utilizing contactless methods. In this way, the monitoring system 10 is spaced from the patient. In the illustrated example, the monitoring system 10 is coupled to a ceiling 100 within the patient room 56. The support apparatus 80 may be positioned in a select location of the patient room 56 to be positioned within the first field of view 18 and the second field of view 24 of the monitoring system 10.

The monitoring system 10 includes a monitor assembly 110 that has a housing 112 coupled to a surface, such as the ceiling 100, in the patient room 56. The housing 112 may also be coupled to a wall surface without departing from the teachings herein. A connector 114 extends from the housing 112 to a support plate 116. The connector 114 may be stationary, or alternatively, may include an actuator 118 that adjusts a position of the support plate 116 relative to the housing 112.

The monitor assembly 110 includes an ambient temperature sensor 130 coupled to the support plate 116. The ambient temperature sensor 130 is configured to sense an ambient temperature within the patient room 56. The ambient temperature may be utilized by the monitoring system 10 to monitor a condition of the patient room 56, as well as for determining certain vital signs information 70 of the patient. The temperature within the patient room 56 may also be adjusted in response to the sensed ambient temperature.

The monitoring system 10 also includes a reference tab 132, which is spaced from the support plate 116 by an elongated support 134. The reference tab 132 includes a tab temperature sensor 136 configured to send a temperature of the reference tab 132. The reference tab 132 is utilized as a reference temperature for determining the vital signs information 70 and improving the accuracy of the first imager 12 as described herein. The reference tab 132 extends partially into the first field of view 18 of the first imager 12 and is captured in the first image data 14.

Referring still to FIGS. 2 and 3, the first imager 12 is coupled to the support plate 116. The first imager 12 defines the first field of view 18 that extends away from the monitor assembly 110 and toward the support apparatus 80. The first imager 12 is generally configured as a thermal camera or imager, which is configured to capture thermal imaging (e.g., the first image data 14) within the first field of view 18 by detecting thermal radiation of the patient on the support apparatus 80. In certain aspects, the first imager 12 may be configured as a long wavelength infrared imager (LWIR), which is sensitive to the LWIR spectrum having a wavelength range between about 8 µm and about 14 µm that are generally emitted by human bodies. In a specific example, the first imager 12 may be a thermal 20K pixel camera module. In another specific example, the first imager 12 may be a FLIP Lepton® Camera Module.

The second imager 20 is coupled to the support plate 116 proximate to the first imager 12. The second imager 20 defines the second field of view 24 that extends away from the monitor assembly 110 and toward the support apparatus 80, overlapping with the first field of view 18. Generally, the second imager 20 is configured as a monochromatic imager, which is configured to detect electromagnetic energy in a predefined wavelength spectrum and output monochromatic imaging, such as, for example, grayscale imaging (e.g., the second image data 22) captured within the second field of view 24. According to various aspects, the second imager 20 is configured as a near infrared (NIR) camera operating within the NIR light bandwidth, which generally has a wavelength range between about 750 nm and about 2,500 nm. In various examples, the second imager 20 may operate within the NIR light bandwidth having a wavelength range between about 750 nm and about 1,500 nm. Further, the second imager 20 may operate within the NIR light bandwidth having a wavelength range between about 800 nm and about 900 nm. In certain aspects, the second imager 20 may be sensitive to a light bandwidth of about 850 nm.

In certain aspects, the second imager 20 may be a charge coupled device (CCD), a complementary metal oxide semiconductor (CMOS) imager, or any type of monochromatic camera. In a specific example, the second imager 20 may include at least one AR0522 CMOS image sensor. In an additional or alternative example, the second imager 20 may be a monochromatic 5M pixel camera module.

The second imager 20 includes a bandwidth filter 140 coupled thereto to filter which wavelength of light is received by the second imager 20. The bandwidth filter 140 generally corresponds with the operating bandwidth range of the second imager 20. Accordingly, the bandwidth filter 140 may allow NIR light 28 having a wavelength in a range between about 750 nm and about 2,500 nm. In various examples, the bandwidth filter 140 may allow NIR light 28 having a wavelength in a range between about 750 nm and about 1,500 nm. Further, the bandwidth filter 140 may allow NIR light 28 having a wavelength in a range between about 800 nm to about 900 nm to be received by the second imager 20.

Referring still to FIGS. 2 and 3, the first field of view 18 and the second field of view 24 are each directed to and include the target area 16, which encompasses at least a head and chest region of the patient on the support apparatus 80. In this way, the first field of view 18 and the second field of view 24 at least partially overlap, and the target area 16 falls within an intersecting region of the first field of view 18 and the second field of view 24 to be captured by both the first and second imagers 12, 20. Accordingly, each of the first image data 14 and the second image data 22 includes imaging of at least the head and chest regions of the patient.

Typically, the support apparatus 80 is positioned in a select location in the patient room 56 such that a head portion 144 of the support apparatus 80 is included in the target area 16. It is contemplated that the actuator 118 operably coupled to the connector 114 may adjust the support plate 116, and consequently, the first and second imagers 12, 20, to ensure the target area 16, including the head portion 144 of the support apparatus 80, is included in each of the first and second fields of view 18, 24. The caregiver may confirm the alignment between the monitor assembly 110 and the support apparatus 80 via an application interface 150 (FIG. 19) described in detail herein.

Additionally or alternatively, the controller 30 of the monitoring system 10 may be able to determine if an object within the target area 16 is the head portion 144 of the support apparatus 80 and may automatically adjust the support plate 116 to position the head portion 144 of the support apparatus 80 in the target area 16. The controller 30 may store dimensions and other information for identifying the support apparatus 80. The controller 30 may also identify the position of the support apparatus 80 related to other features within the patient room 56 and/or based on the associated position within a calibrated coordinate grid and operating envelope of the patient room 56. The operating envelope may be defined or programmed into the controller 30 as a predetermined working range defined in relation to the coordinated grid.

Referring still to FIGS. 2 and 3, the monitor assembly 110 also includes the emitter 26 coupled to the support plate 116. The emitter 26 includes a light source 160 configured to emit the light 28 into an area surrounding the monitor assembly 110 to optimize an image quality of at least the second image data 22. The emitter 26 emits the light 28 into the area surrounding the monitor assembly 110 to provide an adequate intensity for capturing at least the second image data 22.

In various aspects, the light source 160 is a NIR light emitting diode (LED) or an array of NIR LEDs. Generally, the light 28 emitted by the emitter 26 is within the operating wavelength of the second imager 20. Therefore, the light 28 may have a wavelength in a range between about 750 nm and about 2,500 nm. In various examples, the second imager 20 may operate within the NIR light bandwidth having a wavelength range between about 750 nm and about 1,500 nm, and the light 28 emitted by the emitter 26 may have a wavelength in a range between about 750 nm and about 1,500 nm. In additional examples, when the second imager 20 operates within the NIR light bandwidth having a wavelength range between about 800 nm and about 900 nm, the light 28 may have a wavelength in a range from about 800 nm to about 900 nm. It is contemplated that the emitter 26 may continually emit light 28 when the monitoring system 10 is activated to provide illumination for the second imager 20 to continually capture the second image data 22.

The emitter 26 is utilized by the monitoring system 10 to improve the image quality of at least the second image data 22 due to the NIR light 28 being within the operating range of the second imager 20. Moreover, the emitter 26 enables continuous monitoring of the patient during daylight and nighttime conditions. The light 28 emitted from the emitter 26 allows the second imager 20 to capture the second image data 22 regardless of other light conditions within the patient room 56 (e.g., sunlight, nighttime, overhead room light, lamp, etc.).

In certain aspects, multiple emitters 26 may be included in the monitoring system 10. Including multiple emitters 26 may allow for directing light 28 at different angles toward the support apparatus 80, thereby minimizing a shadowing effect on the patient. A shadowing effect may reduce the quality of at least the second image data 22 being captured by the second imager 20. Moreover, each emitter 26 included in the monitoring system 10 may be operably coupled with an actuator 162. The actuator 162 may adjust the position of the emitter 26 independently of the position of the support plate 116 to emit light 28 in a different direction to assist in reducing the shadowing effect on the patient, while not substantially interfering with the first and second fields of view 18, 24.

Figure 4:
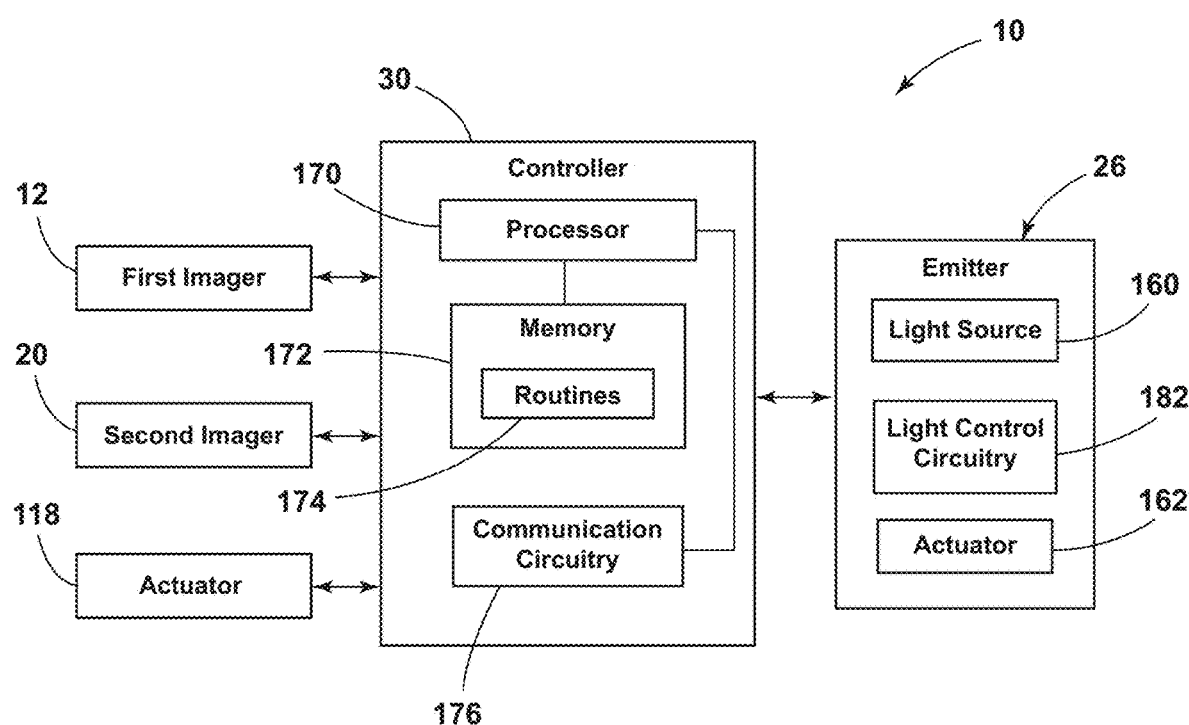
FIG. 4 is a block diagram of a monitoring system, according to the present disclosure.
Figure 14:
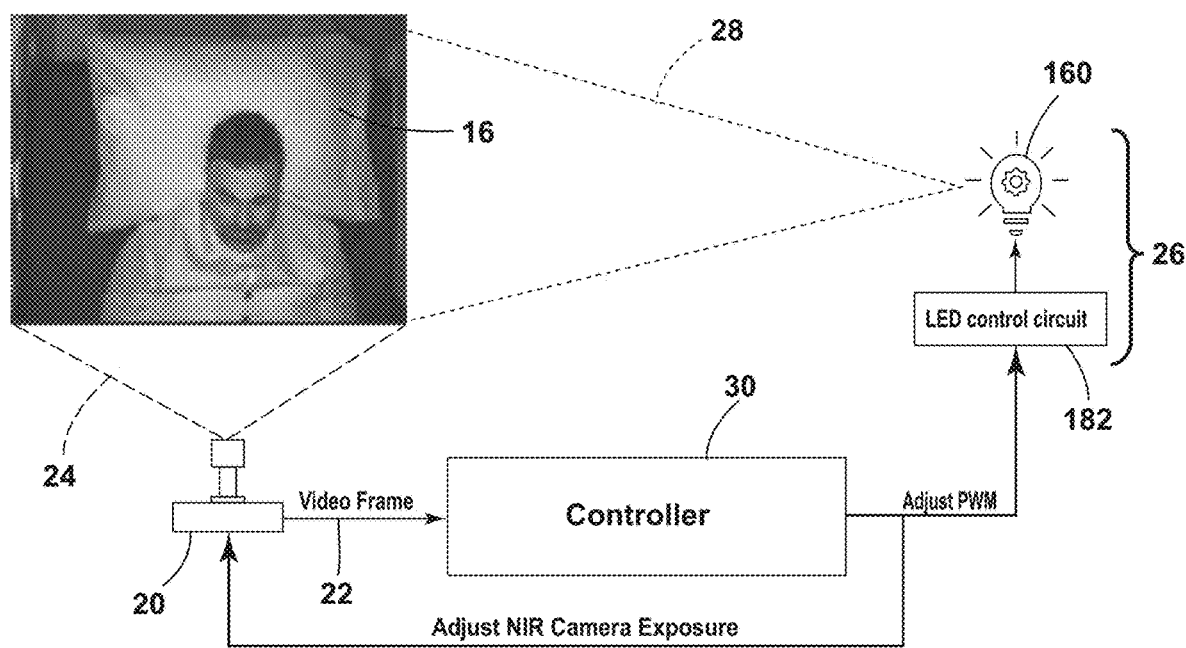
FIG. 14 is a schematic diagram of a monitoring system illuminating a target area and capturing image data within the target area, where the monitoring system adjusts an exposure of an imager and an intensity of emitted light, according to the present disclosure.
Figure 15:
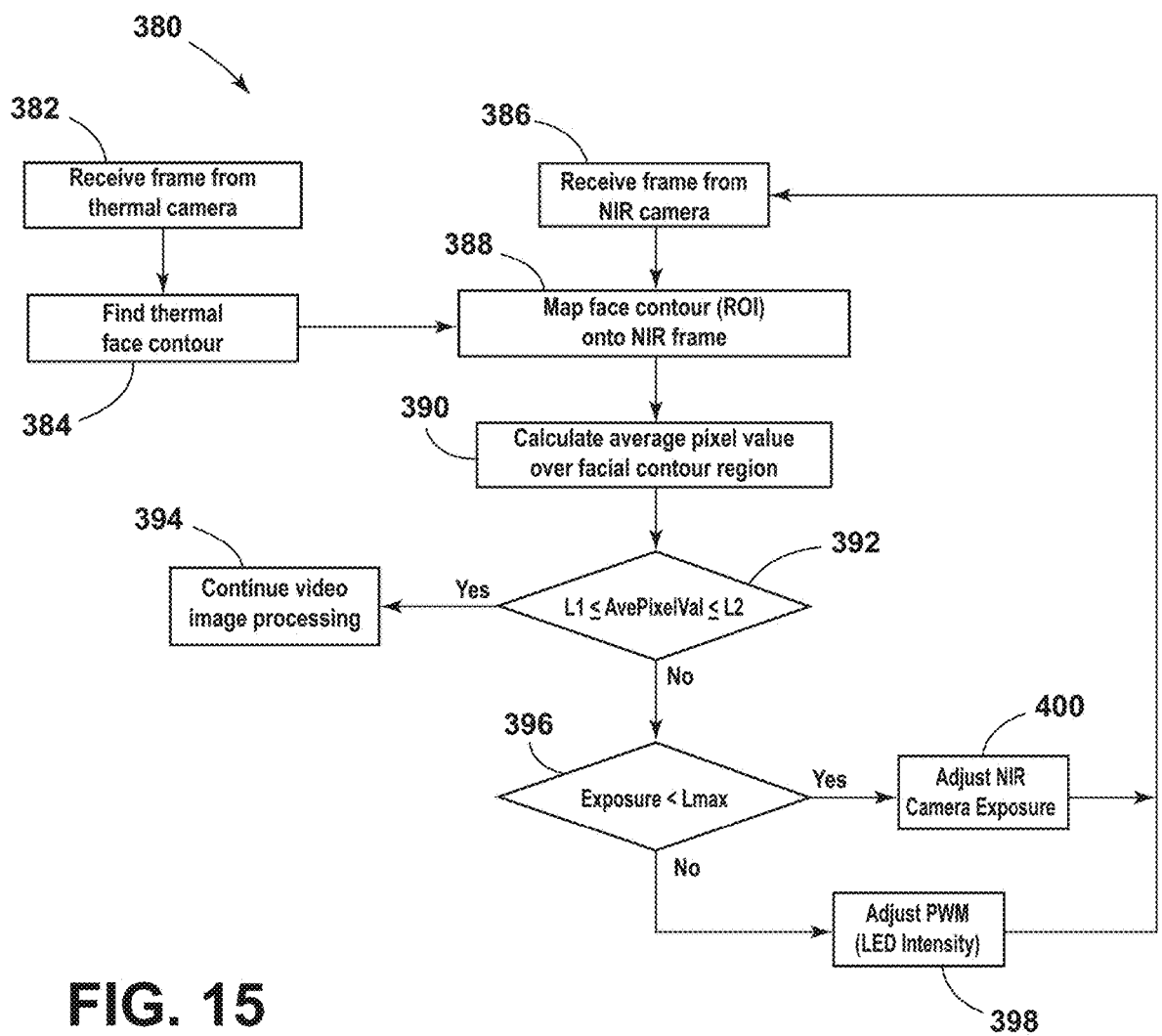
FIG. 15 is a flow diagram of a method of optimizing image quality of image data captured by a monitoring system by adjusting an exposure of an imager and an intensity of emitted light, according to the present disclosure.

Referring to FIG. 4, the monitoring system 10 includes the controller 30, which has a processor 170, a memory 172, and other control circuitry. Instructions or routines 174 are stored within the memory 172 and executable by the processor 170. The control circuitry includes communication circuitry 176 to allow the controller 30 to communicate via a communication network 178 (FIG. 14).

Each of the first imager 12 and the second imager 20 are communicatively coupled with the controller 30. The controller 30 may selectively and independently activate each of the first and second imagers 12, 20 to begin capturing the first and second image data 14, 22, respectively. The first and second image data 14, 22 is continuously or routinely communicated to the controller 30 for processing.

Additionally, the emitter 26 is also communicatively coupled with the controller 30. The emitter 26 generally includes the light source 160 operably coupled with light control circuitry 182. The controller 30 sends a pulse width modulation signal to the light control circuitry 182 to control the intensity of the light 28 emitted by the light source 160. The controller 30 may also communicate with the actuator 162 of the emitter 26 to change the direction of the emitted light 28.

Figure 5:
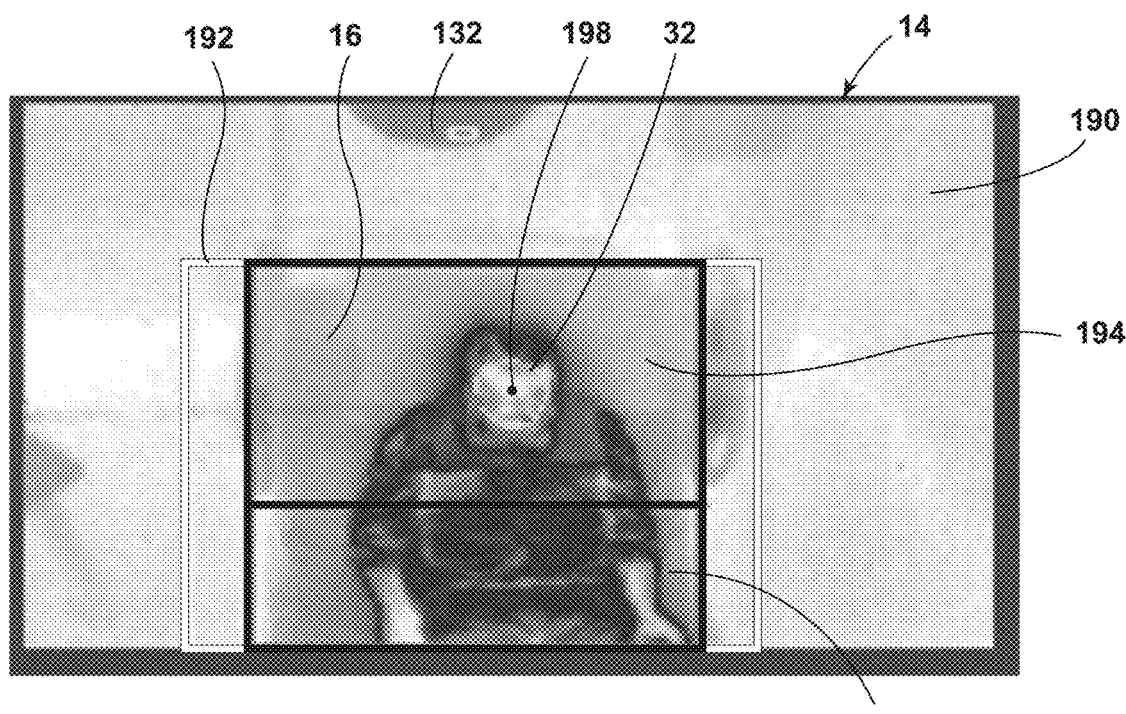
FIG. 5 is representative of a thermal image frame captured by a thermal camera of a monitoring system, according to the present disclosure.

Referring still to FIG. 4, as well as FIG. 5, the first imager 12 is configured to capture multiple thermal image frames 190, which collectively form the first image data 14. Each thermal image frame 190 is communicated to the controller 30 and may be processed independently. The thermal image frames 190 may be captured at predetermined intervals based on a predefined program or instruction 174 from the controller 30. The first imager 12 generally operates at a frame rate, which defines the number of thermal image frames 190 communicated by the first imager 12 to the controller 30 in a predefined period of time. The frame rate may be, for example, 10 frames per second, 30 frames per second, 60 frames per second, etc.

An example of the thermal image frame 190 is illustrated in FIG. 5. Each thermal image frame 190 is an image of the patient at a single point in time. The thermal image frame 190 shows varying thermal radiations from the patient on the support apparatus 80, with discrete portions of the thermal image frame 190 corresponding to discrete temperatures emitted from the patient. Pixels of the thermal image frame 190 may differ based on the discrete temperatures and may be utilized to determine at least some of the vital signs information 70.

The thermal image frame 190 also includes a depiction of the reference tab 132, which extends into the first field of view 18 of the first imager 12. With the reference tab 132 extending into the thermal image frame 190, the first imager 12 may sense or capture a temperature of the reference tab 132. The reference tab 132 and the tab temperature sensor 136 may be utilized for correcting any error in temperature sensed by the first imager 12 as discussed further herein.

Further, the thermal image frame 190 is processed by the controller 30, which may include adding visual indicators to the thermal image frame 190. For example, the controller 30 determines an operating boundary 192 within the thermal image frame 190, which includes at least an upper body of the patient on a portion of the support apparatus 80. The operating boundary 192 coincides with the target area 16 and is utilized to determine regions of interest (ROIs) 194, 196 on the patient. The ROIs 194, 196 define a subset of data in the thermal image frame 190 that is relevant for the purpose of determining the vital signs information 70 of the patient as determined by an object recognition routine 174 of the controller 30.

Utilizing the operating boundary 192, the controller 30 determines the first ROI 194, corresponding with a head and chest zone of the patient, and the second ROI 196, corresponding with a base or mid-section zone of the patient within the thermal image frame 190. The ROIs 194, 196 are narrower than the operating boundary 192 to remove less relevant image data from being processed (i.e., image data 14 without the patient). Utilizing the ROIs 194, 196 and thermal radiation from a face of the patient, the controller 30 determines the facial region 32 of the thermal image frame 190 and a center point 198 of the facial region 32. While the operating boundary 192 and ROIs 194, 196 are visually indicated on the thermal image frame 190 illustrated in FIG. 5, it is contemplated that the controller 30 may process the thermal image frame 190 to determine the operating boundary 192 and ROIs 194, 196 without visibly manipulating the first image data 14.

Figure 6:
FIG. 6 is representative of a grayscale image frame captured by a monochromatic camera of a monitoring system, according to the present disclosure.

Referring still to FIG. 4, as well as FIG. 6, the second imager 20 is configured to capture multiple grayscale image frames 210 or other monochromatic image frames 210. Each grayscale image frame 210 may be independently communicated and processed by the controller 30. The grayscale image frames 210 may be captured at predetermined intervals based on a predefined program or instruction 174 from the controller 30. The second imager 20 generally operates at a frame rate, which defines the number of grayscale image frames 210 communicated by the second imager 20 to the controller 30 in a predefined period of time. The frame rate may be, for example, 10 frames per second, 30 frames per second, 60 frames per second, etc. The frame rate of the second imager 20 is adjustable by the controller 30 as discussed herein.

An example grayscale image frame 210 is illustrated in FIG. 6. Each grayscale image frame 210 is an image of the patient at a single point in time. The controller 30 processes the grayscale image to include multiple visual indicators. The controller 30 determines an operating boundary 212, which coincides with the target area 16. Using the thermal image frame 190, the controller 30 determines a central point 214 on the grayscale image frame 210 that corresponds with the center point 198 on the thermal image frame 190. The controller 30, utilizing the central point 214, determines the facial ROI 34 and two chest ROIs 216, 218. The ROIs 34, 216, 218 define a subset of data in the grayscale image frame 210 that is determined by the object recognition routine 174 and/or an image processing routine 174 of the controller 30 to be relevant to determining the vital signs information 70 of the patient. It is contemplated that the operating boundary 212 and ROIs may not be visible, such that the controller 30 processes the grayscale image frame 210 without visibly manipulating the second image data 22.

Figure 7:
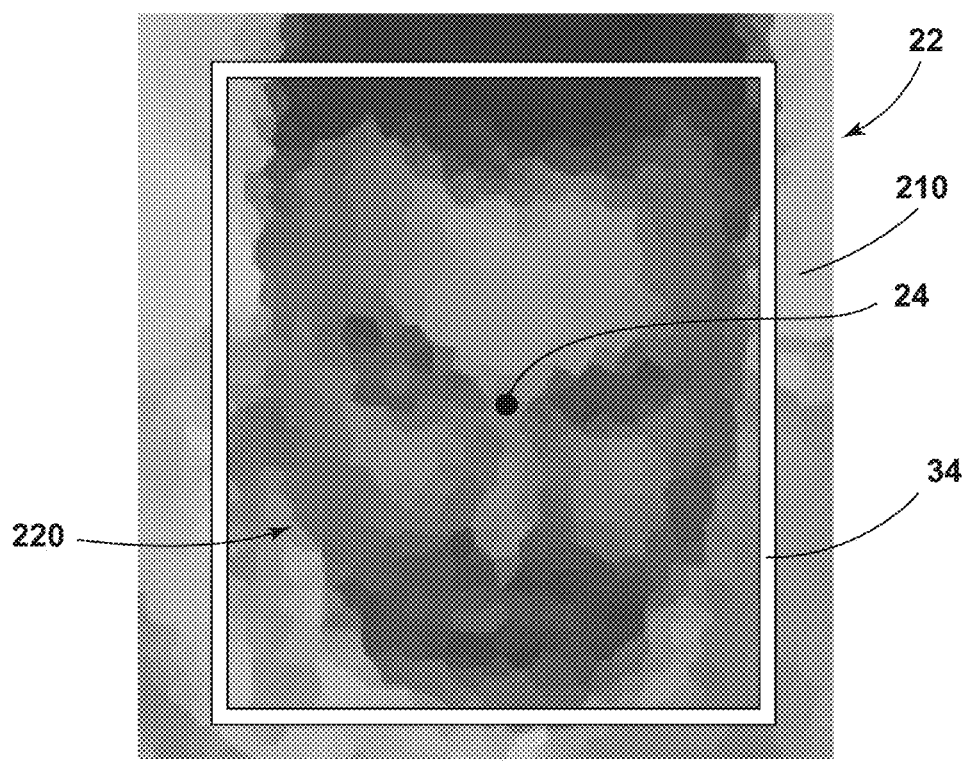
FIG. 7 is an enlarged view of a facial region of interest of a grayscale image frame captured by a monitoring system, wherein the facial region of interest includes a plurality of pixels, according to the present disclosure.

Referring to FIG. 7, the facial ROI 34 of the grayscale image frame 210 is illustrated in isolation from a remainder of the grayscale image frame 210. The grayscale image frame 210 is comprised of pixels 220 and the facial ROI 34 includes a total number of pixels 220, n. Each pixel 220 has a local pixel value, which describes a brightness and/or color that corresponds with the pixel 220. For grayscale images, each pixel 220 has a single pixel value (i.e., a single local pixel value) that corresponds to the brightness of the pixel 220, and the single pixel value generally ranges from about zero, which corresponds to black, to 255, which corresponds to white. The controller 30 utilizes the pixels 220 of the facial ROI 34 to optimize the image quality of the second image data 22 and determine the vital signs information 70 as described in detail herein.

Figure 8:
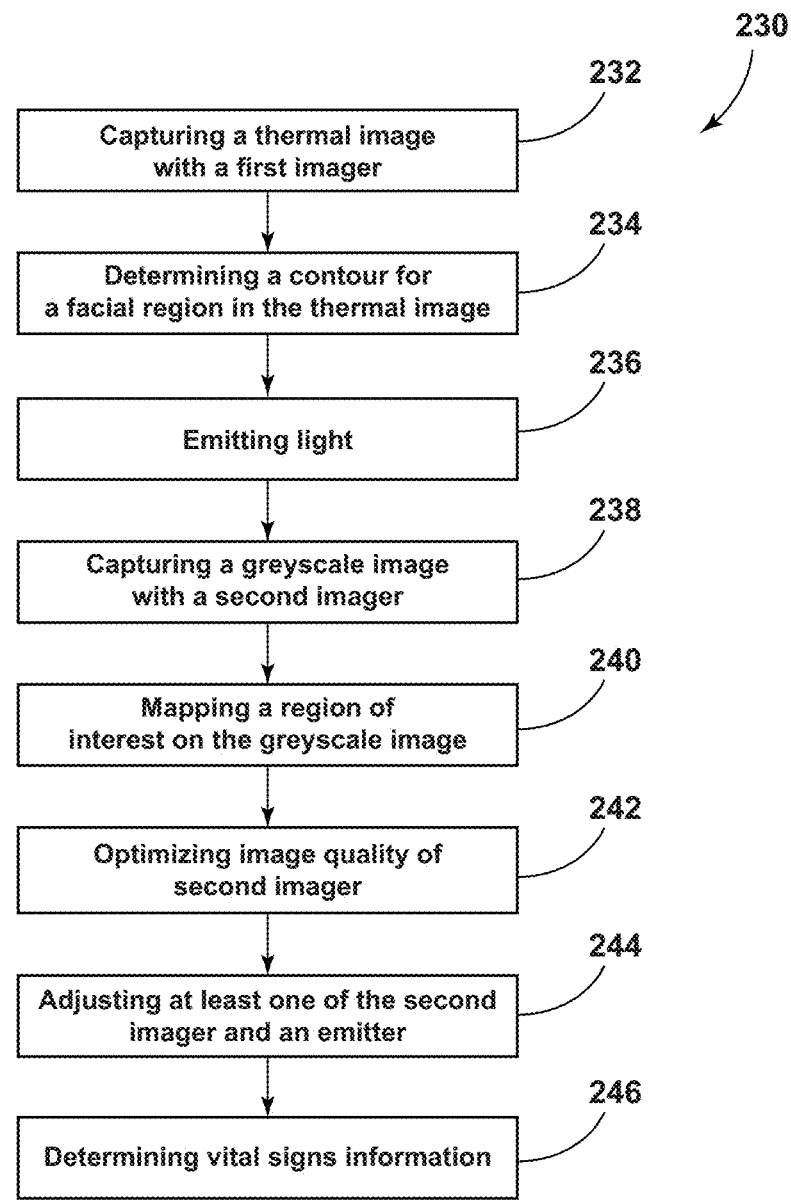
FIG. 8 is a flow diagram of a method of determining patient vital signs information, according to the present disclosure.

Referring to FIG. 8, as well as FIGS. 1-7, the monitoring system 10 provides for remote monitoring of the vital signs information 70 of patients that can be accomplished through a dual imager or dual camera system. The dual imager system allows for contactless monitoring 24/7 once the monitoring system 10 is activated. The contactless monitoring contributes to the safety and comfort of the patient, as well as assists with clinical workflow. For example, the patient may not have to wear a device that monitors certain vital signs and which can cause pressure injuries or discomfort. Additionally, a caregiver may view the vital signs information 70 from a separate location in the medical facility 50, saving time from having to physically obtain the vital signs information 70 from the patient room 56. Each of the first imager 12 and the second imager 20 may continuously send the image data 14, 22 to the controller 30 to be processed at the specific frame rates, allowing continuous monitoring of the patient.

The monitoring system 10 performs a method 230 of monitoring the vital signs information 70 of the patient, which includes step 232 of capturing the thermal image frame 190 (e.g., the first image data 14) with the first imager 12. The thermal image frame 190 is communicated to the controller 30 for processing. In step 234, the controller 30 determines the operating boundary 192 within the thermal image frame 190, which coincides with the target area 16 and is utilized to determine the ROIs 194, 196. The controller 30 determines a contour on the facial region 32 of the thermal image frame 190 within the first ROI 194. The facial thermal radiation enables efficient location of the facial region 32 of the patient in the thermal image frame 190. Utilizing the facial region 32 on the thermal image frame 190, the controller 30 determines the center point 198 of the facial region 32. The controller 30 determines an x-coordinate and a y-coordinate of the center point 198 within the thermal image frame 190. In step 234, the controller 30 may also manipulate the first image data 14 to include the visual indicators of the operating boundary 192, the ROIs 194, 196, and the center point 198.

In step 236, the controller 30 activates the emitter 26 to emit the NIR light 28 into the area surrounding the monitor assembly 110. In step 238, the grayscale image frame 210 (e.g., the second image data 22) is captured by the second imager 20 and communicated to the controller 30 for processing. The emission of the NIR light 28 provides adequate illumination for the second image data 22 to be captured. Additionally, in step 238 the controller 30 determines the operating boundary 212 within the grayscale image frame 210.

In step 240, the controller 30 maps the central point 214 on the grayscale image frame 210 to correspond with the center point 198 on the thermal image frame 190. The central point 214 may be mapped onto the grayscale image frame 210 utilizing geometric transformation. Geometric transformation may be utilized to scale or adjust coordinates of the thermal image frame 190 with coordinates of the grayscale image frame 210 to align the center point 198 of the facial region 32 from the thermal image frame 190 with the central point 214 on the grayscale image frame 210. The controller 30 may also utilize the operating boundaries 192, 212 and common pixels 220 within the operating boundaries 192, 212 to map the central point 214.

Additionally, in step 240, using the central point 214 of the grayscale image frame 210, the controller 30 determines the facial ROI 34, illustrated as a rectangle around the face of the patient in the grayscale image frame 210. It is contemplated that the facial ROI 34 may be an irregular shape or another geometric shape extending over the face of the patient. The controller 30 may also determine two chest ROIs 216, 218 utilizing the coordinates of the central point 214 on the grayscale image frame 210. The first chest ROI 216 is positioned over a left side of the chest of the patient, and the second chest ROI 218 is positioned over a right side of the chest of the patient. In step 240, the controller 30 may also manipulate the second image data 22 to include the visual indicators of the operating boundary 212, the ROIs 34, 216, 218, and the central point 214.

In step 242, the monitoring system 10 optimizes the image quality of the second image data 22 by processing and analyzing the pixels 220 in the grayscale image frame 210, as discussed in detail further herein. If controller 30 determines that the image quality is to be adjusted, the monitoring system 10 adjusts at least one of the second imager 20 and the emitter 26 to optimize the image quality in step 244. The controller 30 is configured to determine whether the vital signs information 70 can be determined from the second image data 22, such as by determining clarity, focus, positioning of the patient, etc. In certain aspects, the controller 30 determines that the image quality is to be adjusted if the controller 30 cannot determine the vital signs information 70 from the second image data 22.

If the image quality is sufficient to analyze for the vital signs information 70, the controller 30 may skip step 244 and proceed to step 246, where the controller 30 utilizes at least one of the first image data 14 and the second image data 22 to determine the vital signs information 70 of the patient. Alternatively, the controller 30 may adjust at least one of the second imager 20 and the emitter 26 in step 244 and then proceed to step 246 when the image quality is sufficient for processing. In various aspects, the vital signs information 70 includes, but is not limited to, a heart rate, a respiration rate, and a facial temperature.

In step 246, the vital signs information 70 may be determined by comparing the pixel value of the pixels 220 in the facial ROI 34 in the grayscale image frame 210. Further, the controller 30 may use multiple grayscale image frames 210, each processed in a similar manner, captured by the second imager 20 to determine the vital signs information 70 and a change in vital signs information 70 over a period of time. Additionally, in step 246, the controller 30 may be configured to communicate the vital signs information 70 to the caregiver. The controller 30 may also be configured to generate an alert relating to the vital signs information 70 when the vital signs information 70 or a change in the vital signs information 70 is outside a predefined range or a predefined change range, respectively. It is understood that the steps of method 230 may be performed in any order, simultaneously, repeated, and/or omitted without departing from the teachings herein.

Figure 9:
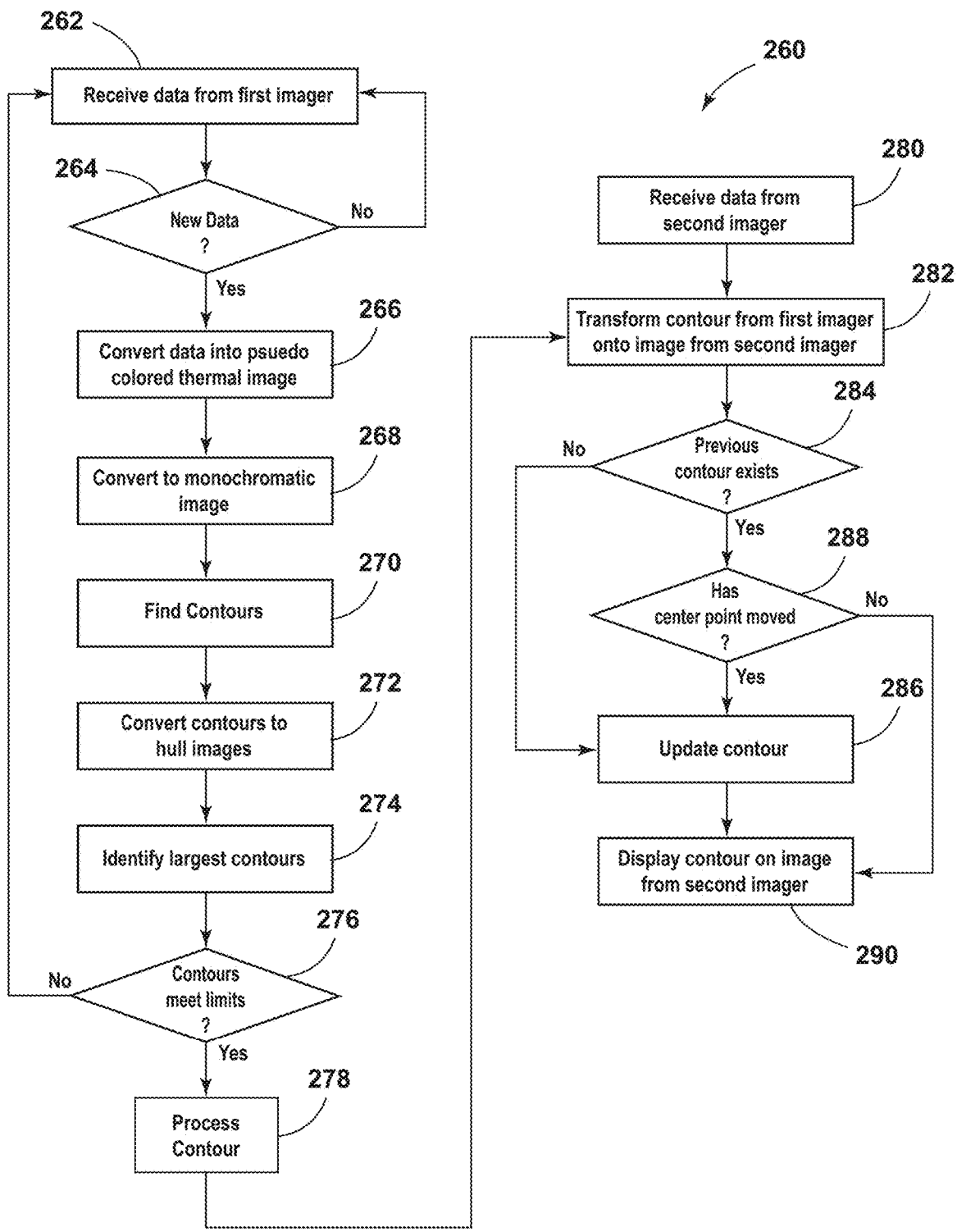
FIG. 9 is a flow diagram of a method of acquiring and processing image data in a monitoring system, according to the present disclosure.

Referring to FIGS. 8 and 9, step 240 of method 230 of identifying and mapping the facial ROI 34 on the grayscale image frame 210 may be accomplished via at least one routine 260, included in routines 174 of the controller 30, directed to image acquisition and processing. In step 262 of the routine 260, the controller 30 receives the thermal image frame 190. In decision step 264, the controller 30 determines whether the thermal image frame 190 is new data. The controller 30 may compare the thermal image frame 190 with previous thermal image frames 190 to determine whether there is new data to be analyzed. If not, such that the thermal image frame 190 was previously processed, the controller 30 returns to step 262 to receive a new thermal image frame 190 to process.

Additionally, in step 264, the controller 30 may utilize the reference tab 132 to correct any temperature errors of the first imager 12. The reference tab 132 extends into the first field of view 18 and is included in the thermal image frame 190. The tab temperature sensor 136 may communicate a sensed reference tab temperature to the controller 30. The sensed tab temperature may be compared to the temperature captured within the thermal image frame 190 and is utilized to correct any temperature error in the detected temperature obtained within the first image data 14. It is contemplated the ambient temperature may also be used to calibrate the first imager 12. If any calibration or corrections occur, the routine 260 may return to step 262 to receive a new thermal image frame 190 for processing.

Returning to decision step 264, if the thermal image frame 190 is new image data, the controller 30 proceeds to step 266 where the first image data 14 received from the first imager 12 is converted into a pseudo colored thermal image. Generally, thermal images are monochromatic images. The monochromatic thermal image frame 190 may be converted to a pseudo thermal image by normalizing the image data and applying a color map, which is stored within the controller 30. The pseudo thermal image may be advantageous for further differentiating the detected thermal radiations depicted in the thermal image frame 190.

In step 268, the controller 30 creates a converted thermal image frame 190 where the thermal image frame 190 from step 266 is converted into a monochromatic image. Adjusting the thermal image frame 190 from the original monochromatic image, to a pseudo colored thermal image, and to a new monochromatic image may enhance the contrast between different detected thermal radiations. In converting the thermal image frame 190, pixels of the thermal image frame 190 with data values closest to a predefined maximum data value are white and the other pixels are black. The predefined maximum data value may be stored within the controller 30.

In step 270, the controller 30 analyzes the converted thermal image frame 190 to find contours. A contour is generally an outline that represents the shape or form of an object. The controller 30 includes at least one routine 174 directed to contour detection and attempting to extract curves representing object shapes from the first image data 14 received from the first imager 12. The contours may be detected through intensity differences in the pixels within the monochromatic image from step 268.

In step 272, the controller 30 converts the contours into convex hull shapes, which simplifies the thermal image frame 190 for processing. Generally, convex hull shapes are the smallest convex set that contains a subset, which is typically the contour. In step 274, the controller 30 analyzes the convex hull shapes to identify the largest contour. Typically, the controller 30 processes the head portion 144 of the support apparatus 80 first. If the contours are not identified in the head portion 144, the controller 30 processes a lower portion of the support apparatus 80 within the operating boundary 192.

Once a contour is identified, in decision step 276, the controller 30 determines whether the identified contour meets predefined limits. The predefined limits are generally hard-coded maximum and minimum size criteria stored within the controller 30. If the identified contour does not meet the predefined limits, the controller 30 returns to step 262 to receive a new thermal image frame 190. Returning to decision step 276, if the identified contour falls within the predefined limit (i.e., within the hard-coded maximum and minimum size criteria), the controller 30 proceeds to step 278 to process the identified contour. The identified contour generally aligns with the facial region 32 (e.g., a thermal facial contour) as the facial thermal radiation often provides the largest contour.

In step 280, the controller 30 receives the grayscale image frame 210 from the second imager 20. In step 282, the controller 30 utilizes the grayscale image frame 210 from step 280 and the processed contour from step 278 to transform the contour from the thermal image frame 190 onto the grayscale image frame 210. The controller 30 identifies coordinates in each of the thermal image frame 190 and the grayscale image frame 210. The controller 30 then transforms the identified contour from the coordinates identified in the thermal image frame 190 onto the coordinates of the grayscale image frame 210. The contour generally includes the central point 214 and the facial ROI 34 (e.g., the rectangular visual identifier) mapped onto the grayscale image frame 210.

The transformation is accomplished by scaling the identified contour. Generally, the scaling is accomplished by a ratio of a resolution of the second imager 20 divided by a resolution of the first imager 12 and shifting each point by Cartesian X and Y offsets, which are determined by common pixels 220 within an intersecting area of the fields of view 18, 24. It is contemplated that the controller 30 may include one or more routines 174 for utilizing geometric transformations to transform the contour from the thermal image frame 190 onto the grayscale image frame 210.

In decision step 284, the controller 30 processes the transformed data and determines whether a previous contour exists in the coordinates on the grayscale image frame 210. If the previous contour does not exist, the controller 30 proceeds to step 286 to add or update the contour on the grayscale image frame 210. Once updated, the controller 30 proceeds to step 288 of displaying the contour on the grayscale image frame 210.

Returning to decision step 284, if the previous contour does exist within the coordinates, the controller 30 proceeds to step 290 to determine whether a coordinate of the center point 198 of the identified contour (e.g., the facial region 32) on the thermal image frame 190 has moved by a predefined number of pixels. If the coordinate of the center point 198 has moved by the predefined number of pixels, the controller 30 proceeds to step 286 of updating the contour on the grayscale image frame 210. Accordingly, if the patient moved, thereby moving the center point 198, the grayscale image frame 210 may be updated and remapped with each movement of the patient. Returning to decision step 284, if the coordinate of the center point 198 has not moved by the predefined number of pixels, the controller 30 proceeds to displaying the previous contour on the grayscale image frame 210 in step 288.

Referring still to FIG. 8, as well as to FIGS. 10-15, in step 242 of method 230, the monitoring system 10 is configured to optimize the image quality of the second image data 22. The controller 30 may include multiple routines 174 for optimizing the image quality utilizing different methods or processes. The optimizing routines 174 may be accomplished independently of the image acquisition routine 260 in FIG. 9, and therefore may include several overlapping steps directed to image data processing. Alternatively, the optimizing routines 174 may be performed concurrently with or immediately after the image acquisition routine 260 illustrated in FIG. 9, in which overlapping steps may be omitted. The optimizing routine 174 may be chosen by the caregiver or may be chosen by the controller 30 in response to the grayscale image frame 210. The image quality may be analyzed by the controller 30 to determine whether the contrast between the pixels 220 in the grayscale image frame 210 is sufficient (e.g., clear, focused, etc.) to determine the vital signs information 70. Optimizing the grayscale image frame 210 may be advantageous for improving the accuracy of the vital signs information 70 determined by the monitoring system 10.

Figure 10:
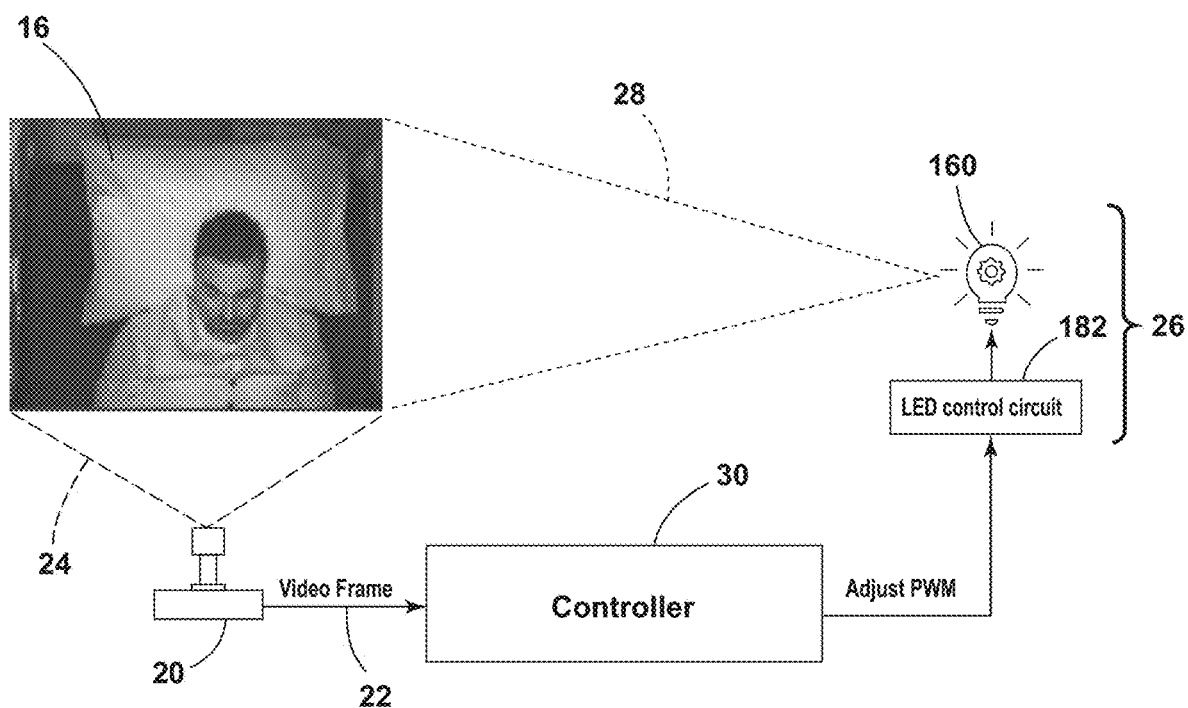
FIG. 10 is a schematic diagram of a monitoring system illuminating a target area and capturing image data within the target area, where the monitoring system adjusts an intensity of emitted light, according to the present disclosure.
Figure 11:
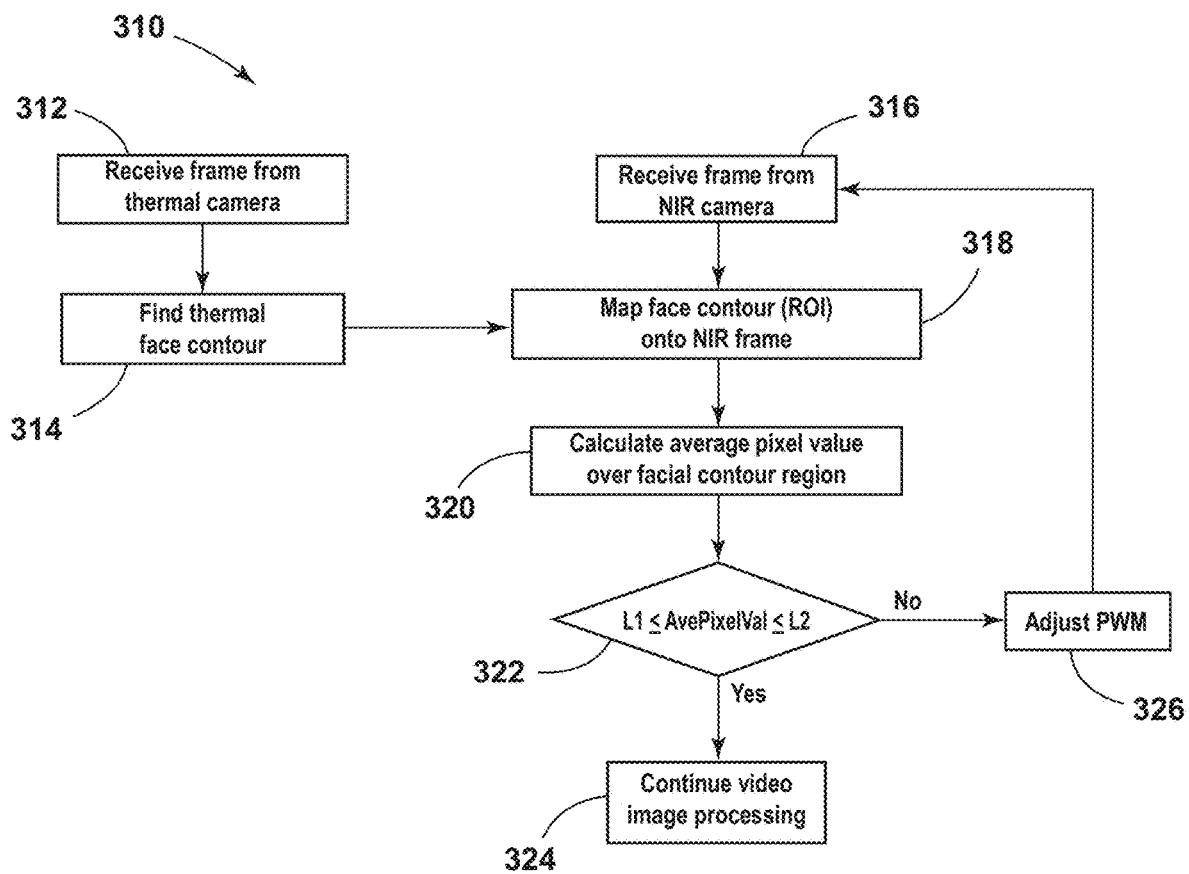
FIG. 11 is a flow diagram of a method of optimizing image quality of image data captured by a monitoring system by adjusting an intensity of emitted light, according to the present disclosure.
Figure 12:
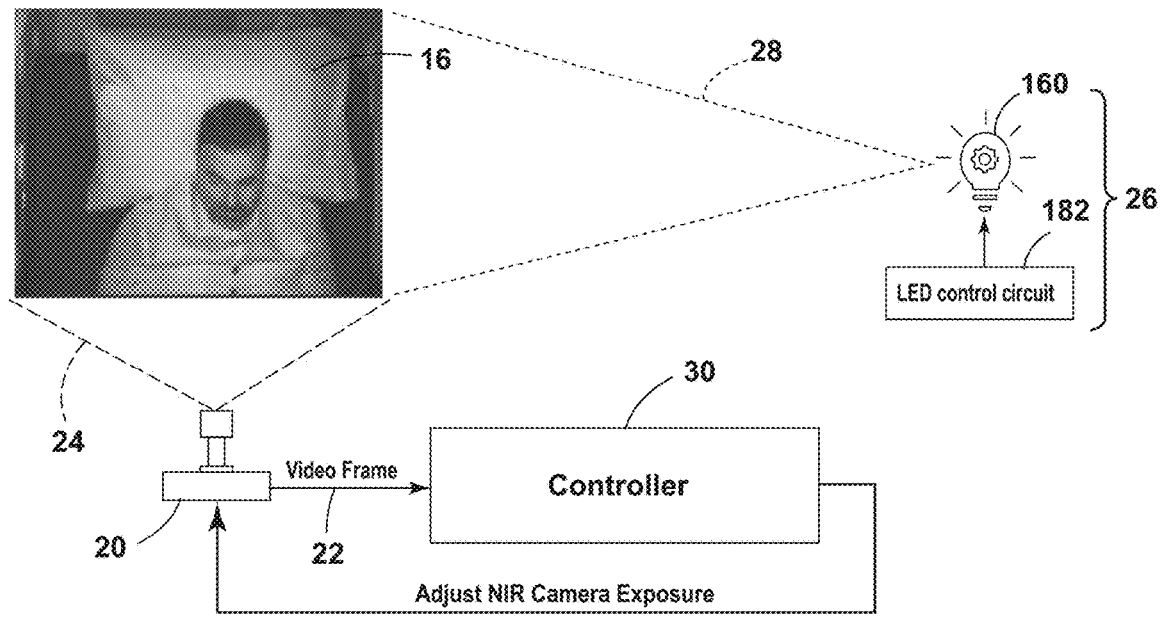
FIG. 12 is a schematic diagram of a monitoring system illuminating a target area and capturing image data within the target area, where the monitoring system adjusts an exposure of an imager, according to the present disclosure.
Figure 13:
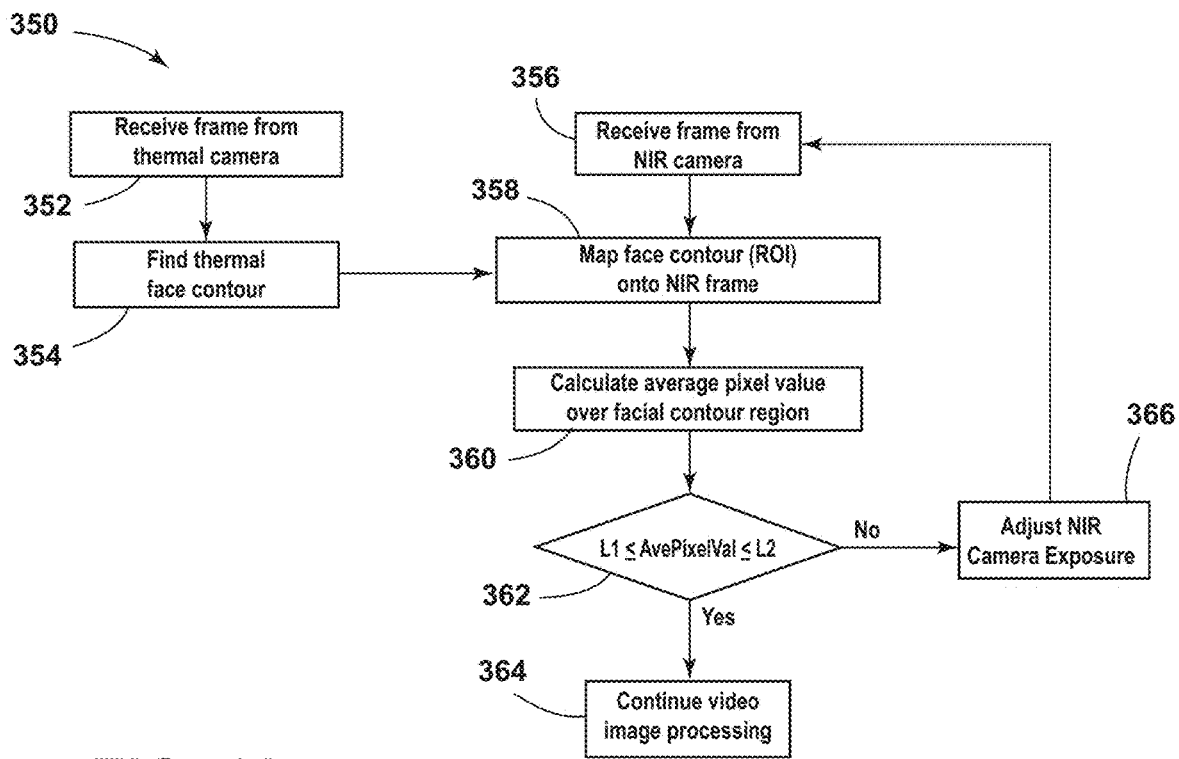
FIG. 13 is a flow diagram of a method of optimizing image quality of image data captured by a monitoring system by adjusting an exposure of an imager, according to the present disclosure.

Referring still to FIGS. 10 and 11, the light source 160 is utilized to illuminate the target area 16 with NIR light 28. The target area 16 falls within the field of view 24 of the second imager 20, which captures the second image data 22 (e.g., the grayscale image frames 210) of the target area 16. The grayscale image frame 210 is communicated to and processed by the controller 30. If the image quality is insufficient, as determined by the controller 30, the controller 30 adjusts the intensity of the light 28.

The controller 30 includes at least one routine 310, included in routines 174, for optimizing the image quality of the second image data 22 by adjusting the intensity of the light 28 emitted from the emitter 26. In step 312 of the routine 310, the controller 30 receives the thermal image frame 190 (e.g., the first image data 14) captured by the first imager 12. In step 314, the controller 30 is configured to process the thermal image frame 190 to identify the contour that corresponds with the facial region 32, similar to the routine 260 described in relation to FIG. 9.

In step 316, the controller 30 receives the grayscale image frame 210 (e.g., the second image data 22) captured by the second imager 20. Utilizing the processed thermal image frame 190 and the grayscale image frame 210, the routine 310 proceeds to step 318 where the controller 30 processes the grayscale image frame 210 to map the facial contour from the thermal image frame 190 onto the grayscale image frame 210, similar to the process described in relation to FIG. 9. The controller 30 determines the facial ROI 34 on the grayscale image frame 210 utilizing the mapped central point 214. The facial ROI 34 is generally the area on the grayscale image frame 210 that encompasses the face of the patient.

In step 320, the controller 30 analyzes the pixels 220 within the facial ROI 34 in the grayscale image frame 210. The controller 30 calculates a total number of pixels 220, n within the facial ROI 34. The controller 30 determines the local pixel value for each pixel 220. As previously stated, for grayscale images, each pixel 220 has a single pixel value that corresponds to the brightness of the pixel 220.

Further, when processing the grayscale image frame 210, the controller 30 calculates a pixel value within the facial ROI 34. The calculated pixel value may be an average pixel value within the facial ROI 34. To calculate the average pixel value, the controller 30 uses the following equation:

$$AvePixelVal = \frac{1}{n} \cdot \sum_{k=1}^{n} P_k,$$

where AvePixelVal or $P_{avg}$ is the average pixel value, $P_k$ is the local or individual pixel value in the facial ROI 34, and n is a total number of pixels 220 in the facial ROI 34. The controller 30 sums the pixel values for each pixel 220 (e.g., from k=1 to k=n) in the facial ROI 34 and divides the summed value by the total number of pixels 220, n, within the facial ROI 34. It is contemplated that the controller 30 may utilize other practicable calculated pixel values without departing from the teachings herein.

In decision step 322, the controller 30 compares the calculated average pixel value, $P_{avg}$, with a predetermined pixel value range, which is stored within the controller 30. The predetermined pixel value range may be the range in which the contrast between the pixels 220 is sufficient for determining the vital signs information 70. The predetermined pixel value range is defined between and includes a lower pixel value, L1, and an upper pixel value, L2. Generally, the average pixel value, $P_{avg}$, being within the predetermined pixel value range ensures that the intensity of the pixel value is within a dynamic range of a sensor of any imager or camera, including the second imager 20. The dynamic range of the sensor is the response or output from the sensor versus the illumination from the face of the patient. The lower pixel value, L1, and the upper pixel value, L2, are utilized to ensure that the monitoring system 10 is not operating in the noise of the signal generated by the sensor, nor saturating the sensor regardless of a change in illumination. If the average pixel value, $P_{avg}$, is greater than or equal to L1 and less than or equal to L2, the controller 30 proceeds to step 324 where the grayscale image frame 210 is processed to determine the vital signs information 70 of the patient.

Returning to decision step 322, if the average pixel value, $P_{avg}$, is less than L1 or greater than L2 (i.e., outside the predetermined pixel value range), the controller 30 proceeds to step 326 to adjust the intensity of the light 28 emitted by the emitter 26 to optimize the image quality. The change in the intensity of the light 28 provides greater contrast in the pixels 220 by providing adequate illumination and preventing saturation of the pixels 220. When the pixels 220 are saturated, the second imager 20 is responding at the maximum pixel value for the saturated pixels 220, reducing pixel contrast.

The controller 30 sends the pulse width modulation signal to the light control circuitry 182 within the emitter 26 to adjust the intensity of the light 28 emitted into the target area 16. The controller 30 may store information that relates pulse width modulation values to average pixel values, $P_{avg}$, to determine the extent that the intensity of the light 28 is to be adjusted. Accordingly, the degree to which the intensity of the light 28 is adjusted may correspond with whether the average pixel value, $P_{avg}$, is less than L1, whether the average pixel value, $P_{avg}$, is greater than L2, and/or the extent to which the average pixel value, $P_{avg}$, is outside the predetermined pixel value range.

Once the controller 30 has adjusted the intensity of the light 28 emitted by the emitter 26, the routine 310 returns to step 316 to receive another grayscale image frame 210. The subsequently captured grayscale image frame 210 may be processed to determine the facial ROI 34 and the average pixel value, $P_{avg}$, within the facial ROI 34. The controller 30 may continue to adjust the intensity of the light 28 emitted by the emitter 26 and capture new grayscale image frames 210 until the average pixel value, $P_{avg}$, within the facial ROI 34 of a subsequently captured grayscale image frame 210 is within the predetermined pixel value range. The power provided to the emitter 26 is adjusted to reach a certain average pixel value, $P_{avg}$, level within the facial ROI 34 that ensures proper illumination of the face of the patient. Moreover, the average pixel value, $P_{avg}$, is utilized as feedback by the monitoring system 10 to adjust the intensity of the light 28 emitted by the emitter 26.

Once the average pixel value, $P_{avg}$, of the subsequently captured grayscale image frame 210 is within the predetermined pixel value range, the controller 30 proceeds to step 324 for processing the grayscale image frame 210 to determine the vital signs information 70 of the patient. The adjustment of the intensity of the light 28 may be advantageous for scenarios where the face of the patient is spaced from the second imager 20 by a predefined distance that makes capturing details more difficult. The adjustment of the light 28 intensity may also depend on the distance the patient is from the monitor assembly 110.

Referring again to FIGS. 13 and 14, the monitoring system 10 includes at least one routine 350, included in routines 174, directed to adjusting an exposure of the second imager 20 to optimize the image quality of the second image data 22. As schematically depicted in FIG. 14, the light source 160 is utilized to illuminate the target area 16 with the NIR light 28. The target area 16 falls within the second field of view 24 of the second imager 20, which captures the second image data 22 (e.g., the grayscale image frame 210) of the target area 16. The grayscale image frame 210 is communicated to and processed by the controller 30. If the image quality is insufficient, as determined by the controller 30, the controller 30 adjusts the exposure of the second imager 20. In such processes, the intensity of the light 28 emitted from the emitter 26 remains fixed.

The exposure of the second imager 20 may be adjusted to optimize the image quality of the second image data 22 to enable continuous monitoring of the patient. As previously stated, the second imager 20 operates at a frame rate for sending consecutive grayscale image frames 210 to the controller 30. For example, the second imager 20 may have a frame rate of 30 frames per second. In such examples, a time difference between two consecutive grayscale image frames 210 is approximately 33 ms. This time difference corresponds to a maximum allowable exposure, $L_{max}$, of the second imager 20. The exposure generally determines how light or dark the image data 22 appears. Depending on the intensity of the light 28 emitted by the emitter 26, the maximum allowable exposure, $L_{max}$, could saturate the grayscale image frame 210, providing minimal or no significant pixel value variations. Without the pixel value variations, the video monitoring system 10 may have decreased accuracy in determining the vital signs information 70 from the second image data 22.

The controller 30 receives the thermal image frame 190 in step 352 and determines the thermal facial contour in step 354. In step 356, the controller 30 receives the grayscale image frame 210, and in step 358, maps the facial ROI 34 on the grayscale image frame 210. Additionally, in step 360, the controller 30 calculates the average pixel value, $P_{avg}$, in the facial ROI 34. In decision step 362, the controller 30 determines whether the average pixel value, $P_{avg}$, is within the predetermined pixel value range. If the average pixel value, $P_{avg}$, is greater than or equal to L1 and less than or equal to L2, the routine 360 proceeds to step 364 of processing the second image data 22 to determine the vital signs information 70 of the patient.

Returning to decision step 362, if the average pixel value, $P_{avg}$, is less than L1 or greater than L2, the controller 30 proceeds to step 366 to adjust the exposure of the second imager 20. The exposure may be adjusted by adjusting a shutter speed or the frame rate of the second imager 20. Generally, the shutter speed dictates the amount of light 28 to which each image frame 210 is exposed. Therefore, increasing the shutter speed of the second imager 20 decreases the exposure. In the example where the second imager 20 has a frame rate of 30 frames per second, with a decreased exposure, the light 28 may not saturate the pixels 220 within the grayscale image frame 210, thereby allowing for greater contrast between the pixels 220. Depending on the exposure and the maximum allowable exposure, $L_{max}$, the controller 30 may increase or decrease the exposure to obtain adequate pixel contrast for determining the vital signs information 70. The controller 30 generally adjusts the exposure of the second imager 20 to between about 15 ms and about 30 ms to increase pixel value variations in the pixels 220 of the facial ROI 34.

After adjusting the exposure, the controller 30 returns to step 352 to receive another grayscale image frame 210. The controller 30 processes the subsequently captured grayscale image frame 210 and determines whether the average pixel value, $P_{avg}$, is within the predetermined pixel value range. The controller 30 may continue to adjust the exposure of the second imager 20 until the average pixel value, $P_{avg}$, is within the predetermined pixel value range. The controller 30 may continue to activate the second imager 20 to capture additional grayscale image frames 210 until the average pixel value, $P_{avg}$, of the most recently captured grayscale image frame 210 includes the average pixel value, $P_{avg}$, within the predetermined pixel value range. Once the average pixel value, $P_{avg}$, is within the predetermined pixel value range, there is sufficient contrast between the pixels 220, and the controller 30 proceeds to step 364 to process the grayscale image frame 210 to determine vital signs information 70 of the patient.

The exposure is adjusted to reach a certain average pixel value, $P_{avg}$, level within the facial ROI 34 that ensures sufficient pixel contract on the face of the patient in the grayscale image frame 210. Moreover, the average pixel value, $P_{avg}$, is utilized as feedback by the monitoring system 10 to adjust the exposure of the second imager 20. The adjustment of the exposure may also compensate for LED wear over time.

Referring again to FIGS. 14 and 15, the controller 30 may be configured to jointly adjust both the intensity of the light 28 emitted by the emitter 26 and the exposure of the second imager 20 to optimize the image quality of the second image data 22. Similar to the routines 310, 350 described herein, the controller 30 includes at least one routine 380 (included in routines 174) for adjusting both the emitter 26 and the second imager 20 to optimize the image quality obtained by the second imager 20. The controller 30 receives the thermal image frame 190 in step 382 and determines the thermal facial contour in step 384.

In step 386, the controller 30 receives the grayscale image frame 210, and in step 388, maps the facial ROI 34 on the grayscale image frame 210. Additionally, in step 390, the controller 30 calculates the average pixel value, $P_{avg}$, in the facial ROI 34. In decision step 392, the controller 30 determines whether the average pixel value, $P_{avg}$, is within the predetermined pixel value range. If the average pixel value, $P_{avg}$, is greater than or equal to L1 and less than or equal to L2, the routine 310 proceeds to step 394 of processing the second image data 22 to determine the vital signs information 70 of the patient.

Returning to decision step 392, if the average pixel value, $P_{avg}$, is outside of the predetermined pixel value range, the controller 30 proceeds to step 396 of routine 380 to compare the exposure of the second imager 20 to the maximum allowable exposure, $L_{max}$. In decision step 396, if the exposure is less than $L_{max}$, the controller 30 proceeds to step 398 to adjust the exposure of the second imager 20. The controller 30 generally adjusts the shutter speed to increase or decrease the exposure. The controller 30 may increase or decrease the exposure based on the current exposure in combination with the brightness or darkness of the pixels 220. The controller 30 generally adjusts the exposure to between about 15 ms to about 30 ms. After adjusting the exposure, the controller 30 returns to step 382 to activate the second imager 20 to capture and subsequently process a new grayscale image frame 210.

Returning to decision step 396, if the exposure is not less than the maximum allowable exposure, $L_{max}$ (e.g., generally equal to $L_{max}$), the controller 30 adjusts the intensity of the light 28 emitted by the emitter 26 via the pulse width modulation signal in step 400. After adjusting the intensity of the light 28, the controller 30 returns to step 386 to capture and subsequently process a new grayscale image frame 210. The routine 380 continues to adjust at least one of the exposure of the second imager 20 and the intensity of light 28 emitted from the emitter 26 until the average pixel value, $P_{avg}$, within the facial ROI 34 of a subsequently captured grayscale image frame 210 is within the predetermined pixel value range. Once the average pixel value, $P_{avg}$, is within the predetermined pixel value range, the controller 30 proceeds to step 394 to determine the vital signs information 70 of the patient.

Referring to FIGS. 1-15, the monitoring system 10 is configured to determine the vital signs information 70 of the patient through the first and second image data 14, 22. Accordingly, the monitoring system 10 is a contactless method for monitoring a status of the patient. The vital signs information 70 may include the heart rate, the respiration rate, and the facial temperature of the patient. The calculated or average pixel value, $P_{avg}$, for the facial ROI 34 in the second image data 22 may be utilized to determine at least some of the vital signs information 70. Some of the vital signs information 70 may also be determined using the pixels of the facial region 32 of the first image data 14.

For example, pulsatile oxygenated blood flow absorbs NIR light 28. The absorption of the NIR light 28 consequently generates pulsatile pixel variations. These pulsatile pixel variations may be utilized by the controller 30 to determine the heart rate of the patient. The average pixel value, $P_{avg}$, may be compared to the number of grayscale image frames 210 over time to generate data points that may be analyzed and/or processed to determine the heart rate.

The heart rate measurement is generally determined by comparing pixel values in each grayscale image frame 210 over time. The controller 30 is configured to determine the average pixel value, $P_{avg}$, within the facial ROI 34 in each image frame 210 for the heart rate measurement. The controller 30 is configured to determine the data points, which are generally representative of a relationship between the average pixel value, $P_{avg}$, and a number of grayscale image frames 210 over time. The controller 30 is configured to utilize the data points to determine the heart rate of the patient. For example, the data may be detrended and may employ a Fast Fourier Transform. The monitoring system 10 may have any practicable sampling frequency for the heart rate measurement resolution.

In another non-limiting example, the controller 30 is configured to determine the respiration rate of the patient using the pixels 220 in at least one of the chest ROIs 216, 218 in multiple grayscale image frames 210 captured as the second image data 22. The controller 30 determines the average pixel value, $P_{avg}$, within one or both of the chest ROIs 216, 218, which is generally determined similarly as the facial ROI 34 described herein. The chest movements from breathing translate into similar pixel variations over a period of time within the chest ROIs 216, 218. The controller 30 monitors the pixel variations over multiple grayscale image frames 210 to determine the pattern in variation, which corresponds with the respiration rate of the patient.

In an additional non-limiting example, the controller 30 is configured to determine the facial temperature of the patient. The monitoring system 10 generally utilizes the average pixel value, $P_{avg}$, from the facial region 32 in the thermal image frame 190 captured as the first image data 14. The change in temperature may be monitored over multiple thermal image frames 190 by monitoring the change in the average pixel value, $P_{avg}$, overtime. The average pixel value, $P_{avg}$, in the facial region 32 may be calculated similarly to the average pixel value, $P_{avg}$, for the second image data 22 described herein.

Referring still to FIGS. 1-15, movement of the head position of the patient may affect the vital signs information 70. Movement in an x-direction and/or a y-direction may trigger the monitoring system 10 to obtain new data points.

The changes in the x-direction and the y-direction may be determined using the coordinates and/or the change in coordinates of the center point 198 and/or the central point 214.

In order to improve accuracy in the vital signs information 70, the controller 30 follows at least one routine 174 to optimize the image quality of the second image data 22. The image quality of the second image data 22 may be tuned based on the average pixel value, $P_{avg}$, within the facial ROI 34 within the predetermined pixel value range. Either the caregiver or the controller 30 may determine whether the second imager 20, the emitter 26, or both the second imager 20 and the emitter 26 are adjusted. In certain aspects, the quality of the captured image data 22, including contrast between the pixels 220, may determine which aspect or aspects of the monitoring system 10 is adjusted.

The routines 174 disclosed herein to optimize the image quality may be advantageous for when the patient is spaced from the monitor assembly 110. Further, the processes may be advantageous for obtaining the first and second image data 14, 22 regardless of lighting in the medical facility 50. It is contemplated that the steps of the method 230 and routines 174, including routines 260, 310, 350, 380, may be performed in any order, simultaneously, repeated, and/or omitted without departing from the teachings provided herein.

Figure 16:
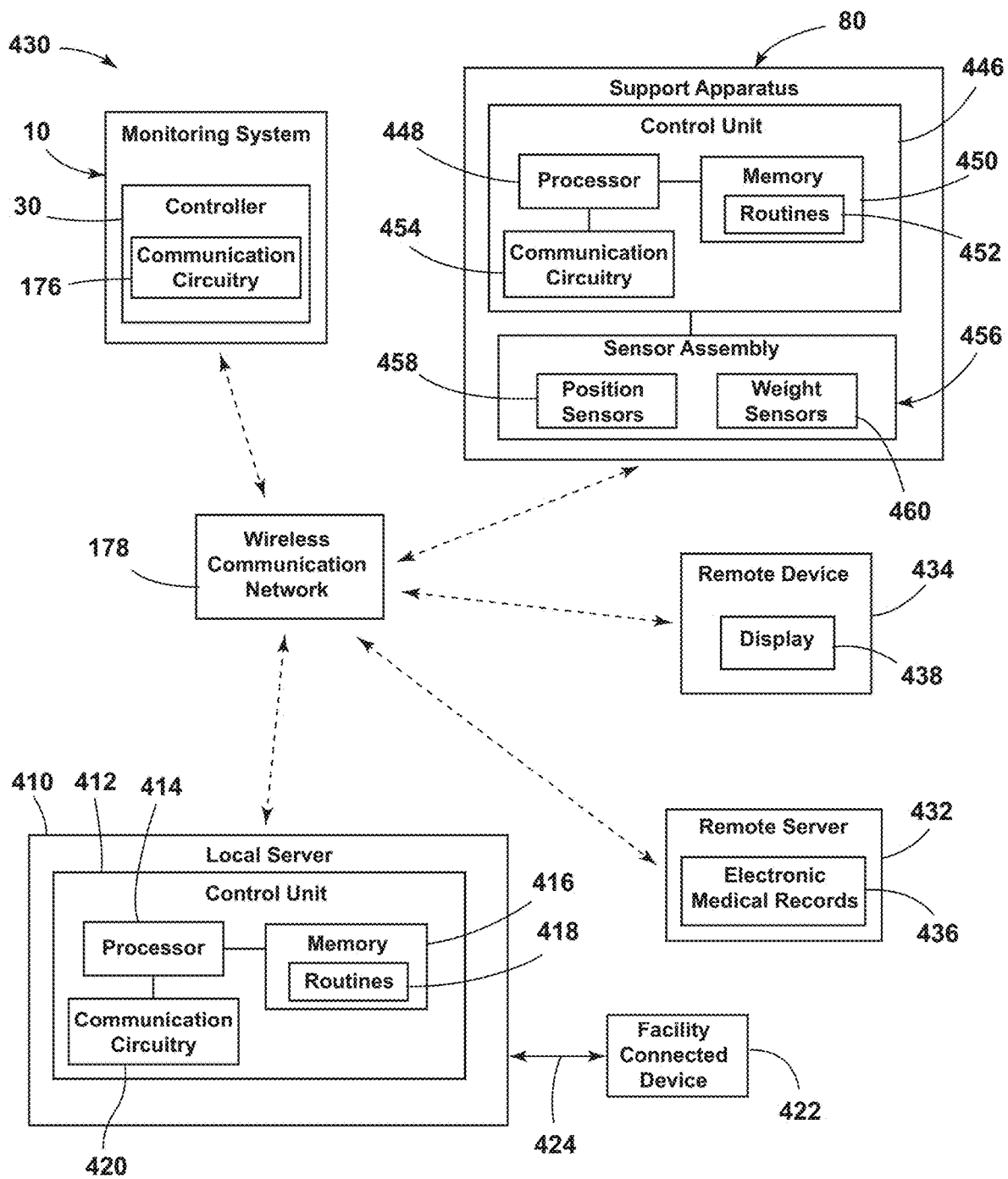
FIG. 16 is a block diagram of an information system of a medical facility, according to the present disclosure.

Referring to FIG. 16, the monitoring system 10 is generally configured to communicate with other systems and devices within the medical facility 50 via the communication network 178. The monitoring system 10 may communicate with a local server 410 of the medical facility 50. The local server 410 generally has a control unit 412 having a processor 414, a memory 416, and other control circuitry. Instructions or routines 418 are stored in the memory 416 and executable by the processor 414. The local server 410 generally includes communication circuitry 420 for communicating via the communication network 178. The local server 410 is also in communication with a facility connected device 422 in the medical facility 50, such as a computer or status board at a nurse call station via Ethernet 424.

The local server 410 includes software (e.g., routines 418) related to an information system 430 of the medical facility 50. In the illustrated example, the information system 430 includes the local server 410, the facility connected device 422, a remote server 432, a remote device 434, the monitoring system 10, and the support apparatus 80. The monitoring system 10 may be at least partially included in at least one of the local server 410 and the remote server 432. The information system 430 provides a system for caregivers to communicate with one another, as well as access and share information regarding the patient. The remote server 432 generally stores electronic medical records 436 or other health records for each patient of the medical facility 50. Such electronic medical records 436 may also be stored within the local server 410. Additionally or alternatively, the remote device 434 generally includes a display 438 for viewing information. The remote device 434 may be associated with the caregiver and may be, for example, a phone, a tablet, a laptop, a wearable device, or other remote feature used for viewing or otherwise obtaining information.

Referring still to FIG. 16, the monitoring system 10 is also in communication with the support apparatus 80 via the communication network 178 and/or direct communication. Information from the support apparatus 80 may be utilized by the monitoring system 10 as a factor in determining vital signs information 70 from the patient. The support apparatus 80 generally includes a control unit 446 having a processor 448, a memory 450, and other control circuitry. Instructions or routines 452 are stored in the memory 450 and executable by the processor 448. The support apparatus 80 also includes communication circuitry 454 for communicating via the communication network 178.

The support apparatus 80 includes a sensor assembly 456 for sensing information about the support apparatus 80 and the patient thereon. In the illustrated example, the sensor assembly 456 includes position sensors 458 for sensing the position of the upper frame 84 such as, for example, the elevated head portion 144. The sensor assembly 456 may also sense a position of each siderail 96, which may indicate a potential egress from the support apparatus 80.

Figure 19:
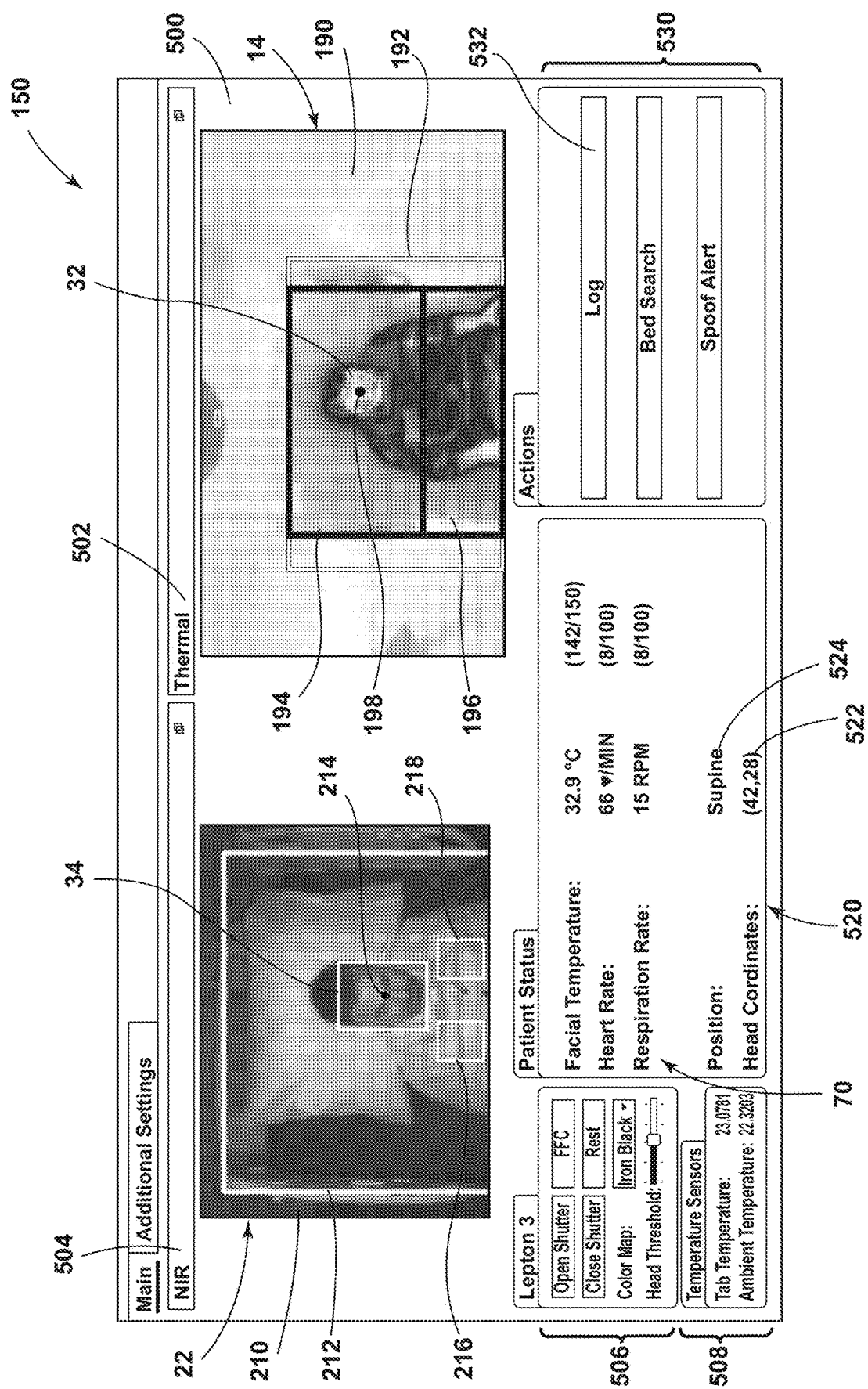
FIG. 19 is representative of an application interface displaying image data and patient information obtained from a monitoring system, according to the present disclosure.

The sensor assembly 456 also includes force or weight sensors 460 for sensing a presence and a position of the patient on the support apparatus 80. The weight sensors 460 may also be utilized as a scale system to monitor a weight of the patient, which may be communicated to the caregiver via the electronic medical record 436 or on the application interface 150 (FIG. 19). The weight sensors 460 may also sense whether an unexpected weight has been added to the support apparatus 80 (e.g., a family member sitting on the support apparatus 80) and provide other data regarding activities surrounding the support apparatus 80.

Additionally, the weight sensors 460 may be utilized to monitor movement of the patient on the support apparatus 80. The movement may be communicated to the controller 30 of the monitoring system 10. The movement may indicate to the monitoring system 10 that the center point 198 and the central point 214 may have moved, initiating new imaging and re-optimization by the monitoring system 10. The position of the support apparatus 80 and the position of the patient are stored within the electronic medical record 436, and may also be communicated to the caregiver via the application interface 150 (FIG. 19).

Referring still to FIG. 16, the sensor assembly 456 may also be associated with a pneumatic system within a mattress or other support feature of the support apparatus 80. The pneumatic system generally includes a plurality of bladders that are independently operable between an inflated condition and a deflated condition via a pump. The sensor assembly 456 may include pressure sensors for sensing a pressure within the bladders and communicating the sensed pressure to the control unit 446.

The pneumatic system may alter the position of the patient on the support apparatus 80 due to various therapies that may be applied. The condition of the bladders may elevate a portion of the body of the patient or apply different pressures to various areas on the patient. Additionally or alternatively, the bladders may be utilized for rotation therapy, which operates to turn the patient along a longitudinal axis in response to inflation and/or deflation of selected bladders. The bladders may be utilized to provide continuous lateral rotation therapy, which continuously adjusts the patient a left side and a right side. Moreover, the bladders may be utilized as a part of a turn assist protocol, which assists the caregiver in turning the patient for back care, dressing changes, and other procedures or treatments. Further, the pneumatic system may include fill bladders that operate to fill a space between adjacent segments 86, 88, 90 of the upper frame 84. The information from pressure sensors of the sensor assembly 456 may be communicated to the control unit 446 to assist in determining the position of the patient. The information from the pressure sensors and the pneumatic system may also communicate continual movement and adjustment of the patient position based on the operation of the pneumatic system, which may affect the imaging of the monitoring system 10.

Referring still to FIG. 16, the communication network 178 may be part of a network of the medical facility 50. The facility network may include a combination of wired connections (e.g., Ethernet 424), as well as wireless connections, which may include the wireless communication network 178. The communication network 178 may include a variety of electronic devices, which may be configured to communicate over various wired or wireless communication protocols. In the illustrated configuration, the monitoring system 10 is in wireless communication with each of the local server 410, the remote server 432, the remote device 434, and the support apparatus 80. The communication network 178 may include a wireless router through which the remotely accessed devices may be in communication with one another, as well as the local server 410.

The communication network 178 may be implemented via one or more direct or indirect nonhierarchical communication protocols, including but not limited to, Bluetooth®, Bluetooth® low energy (BLE), Thread, Ultra-Wideband, Z-wave, ZigBee, etc. Additionally, the communication network 178 may correspond to a centralized or hierarchal communication network 178 where one or more of the devices communicate via the wireless router (e.g., a communication routing controller). Accordingly, the communication network 178 may be implemented by a variety of communication protocols, including, but not limited to, global system for mobile communication (GSM), general packet radio services, code division multiple access, enhanced data GSM environment, fourth generation (4G) wireless, fifth generation (5G) wireless, Wi-Fi, world interoperability for wired microwave access (WiMAX), local area network, Ethernet 424, etc. By flexibly implementing the communication network 178, the various devices and servers may be in communication with one another directly via the wireless communication network 178 or a cellular data connection.

Each of the controller 30 and the control units 412, 446 disclosed herein may include various types of control circuitry, digital or analog, and may each include a processor 170, 414, 448, a microcontroller, an application specific integrated circuit (ASIC), or other circuitry configured to perform the various inputs or outputs, control, analysis, or other functions described herein. The memories 172, 416, 450 described herein may be implemented in a variety of volatile and nonvolatile memory formats. Routines 174, 418, 452 may include operating instructions to enable the various methods described herein.

Figure 17:
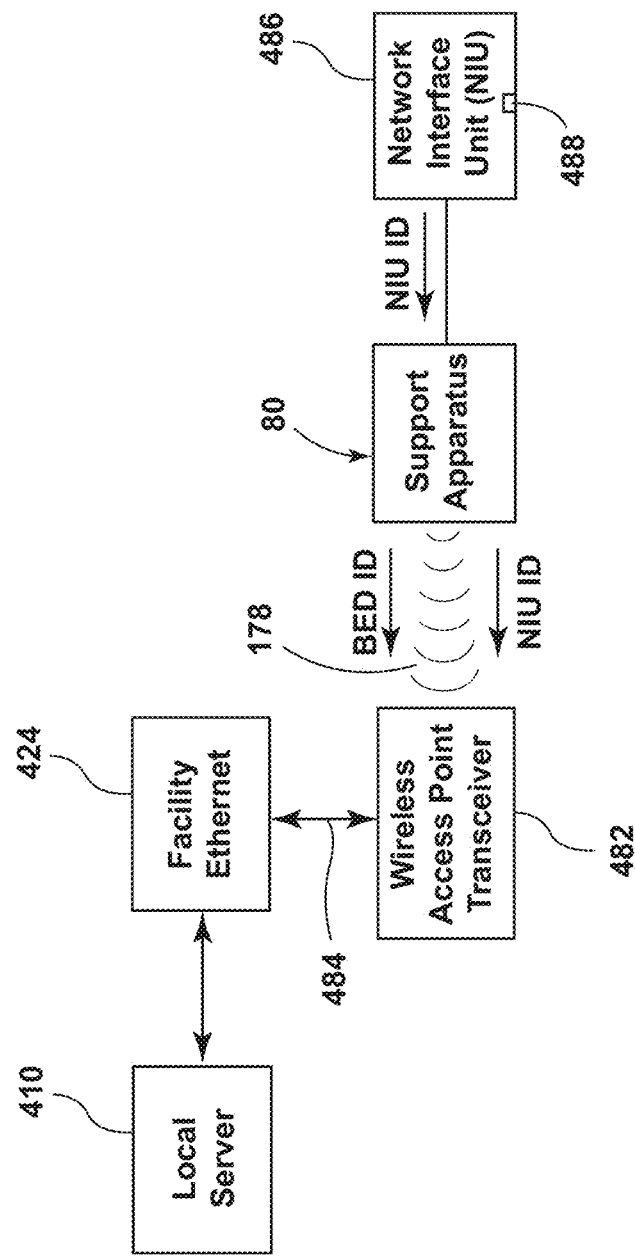
FIG. 17 is a block diagram of a support apparatus wirelessly communicating with a local server via a wireless access point transceiver, according to the present disclosure.
Figure 18:
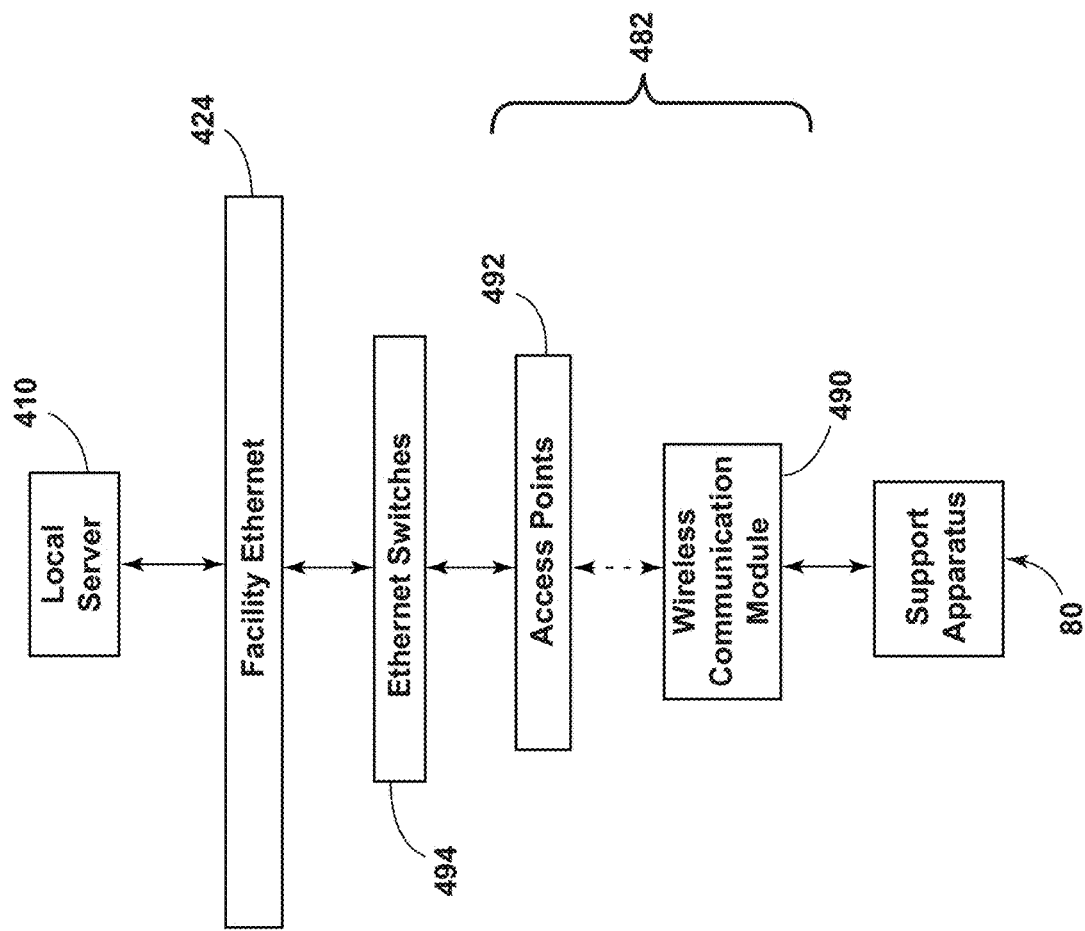
FIG. 18 is a block diagram of a support apparatus wirelessly communicating with a local server via a wireless communication module, according to the present disclosure.

Referring still to FIG. 16, as well as FIGS. 17 and 18, exemplary communications of the support apparatus 80 to the local server 410 are illustrated. The monitoring system 10 may receive information from the support apparatus 80 via the communication network 178 and through the local server 410. In certain aspects, the support apparatus 80 is configured to communicate with a wireless access transceiver 482, which is coupled to Ethernet 424 of the medical facility 50. The communication network 178 provides for bidirectional communication between the support apparatus 80 and the wireless access transceiver 482. The wireless access transceiver 482 communicates bidirectionally with Ethernet 424 via a data link 484.

As illustrated in FIG. 17, the support apparatus 80 may be associated with a network interface unit 486. Multiple network interface units 486 may be provided in various locations within the medical facility 50. Each support apparatus 80 and each network interface unit 486 is assigned a unique identification code, such as a serial number. Various components of the monitoring system 10 and/or the information system 430 on the local server 410 may include software (e.g., routines 418) that operate to associate the identification code of the support apparatus 80 with the network interface unit identification data to locate each support apparatus 80 within the medical facility 50. Each network interface unit 486 includes a port 488 for selectively coupling with Ethernet 424. When the network interface unit 486 is coupled with Ethernet 424, the network interface unit 486 communicates the identification data to the support apparatus 80, which then wirelessly communicates the data for the support apparatus 80 and the network interface unit 486 to the wireless access transceiver 482. The wireless access transceiver 482 then communicates with the local server 410 via Ethernet 424.

As illustrated in FIG. 18, the support apparatus 80 may be capable of communicating wirelessly via a wireless communication module 490. The wireless communication module 490 generally communicates via an SPI link with circuitry of the associated support apparatus 80 (e.g., the communication circuitry 454) and via a wireless 802.11 link with wireless access points 492. The wireless access points 492 are generally coupled to Ethernet switches 494 via 802.3 links. It is contemplated that the wireless communication modules 490 may communicate with the wireless access points 492 via any of the wireless protocols disclosed herein. Additionally or alternatively, the Ethernet switches 494 may generally communicate with Ethernet 424 via an 802.3 link. Ethernet 424 is also in communication with the local server 410, allowing information and data to be communicated between the local server 410 and the support apparatus 80.

Referring again to FIG. 16, as well as to FIG. 19, the monitoring system 10 is in communication with the support apparatus 80 and the remote server 432 to obtain information from the support apparatus 80 and the electronic medical records 436. The monitoring system 10 may compare the currently detected vital signs information 70 with previous vital signs information 70 or may compare the vital signs information 70 with the position of the patient on the support apparatus 80. The monitoring system 10 may compare detected vital signs information 70 with baseline information stored in the electronic medical record 436. Based on the information from the support apparatus 80 and/or the electronic medical record 436, the monitoring system 10 may then trigger an alert to the caregiver based on the detected information. Additionally or alternatively, the monitoring system 10 may combine information from the monitoring system 10, the electronic medical record 436, and/or the support apparatus 80 to be displayed on the application interface 150 for the caregiver.

An exemplary application interface 150 is illustrated in FIG. 19. The application interface 150 includes information from the monitoring system 10 and the support apparatus 80, as well as a way to input and store information in the electronic medical record 436. Each of the remote device 434 and the facility connected device 422 may include an application or software utilized for displaying the application interface 150.

In the illustrated example of FIG. 19, the application interface 150 displays a main or home view 500 associated with the monitoring system 10. The home view 500 includes the thermal image frame 190 and the grayscale image frame 210, each processed by the controller 30. The thermal image frame 190 is included under an identifying title 502 (e.g., "Thermal"). Additionally, in the illustrated example, the thermal image frame 190 includes the operating boundary 192, the first ROI 194, the second ROI 196, and the center point 198 of the facial region 32 visible on the thermal image frame 190.

The grayscale image frame 210 is included proximate to the thermal image frame 190 and under an identifying title 504 (e.g., "NIR"). The grayscale image frame 210 includes the operating boundary 212, the central point 214, the facial ROI 34, and the chest ROIs 216, 218 visible on the grayscale image frame 210. The visibility of the operating boundaries 192, 212 and other visual indicators from the controller 30 allows the caregiver to confirm that the monitoring system 10 is processing appropriate regions on the thermal image frame 190 and the grayscale image frame 210 to obtain the vital signs information 70. The caregiver may also compare the thermal image frame 190 to the grayscale image frame 210 to generally confirm the center point 198 being utilized to map the facial ROI 34. Further, the caregiver may confirm the alignment between the monitor assembly 110 and the support apparatus 80 and that the patient is included in the first and second image data 14, 22. The caregiver may also generally confirm the quality (e.g., focus, clarity, patient position, etc.) of the image frames 190, 210.

The application interface 150 also includes setting information 506 related to at least the first imager 12, which is included under an identifying title (e.g., "Lepton 3"). The setting information 506 includes shutter settings for an open shutter and a closed shutter of the first imager 12. The open shutter settings include flat field correction, which may be utilized to calibrate an image sensor or image sensors within the first imager 12. Other setting information 506 includes a type of color map that is utilized for the first image data 14 and a head threshold. The head threshold may be, for example, a sensitivity for reevaluating the position of the head based on the movement of the patient (e.g., a higher sensitivity results in capturing new image data 14, 22 in response to a smaller degree of movement). Each of the settings may be adjusted by the caregiver via the application interface 150. Additional settings may be accessed and adjusted on a secondary view on the application interface 150 (e.g., in a tab entitled "Additional Settings").

Additionally, the application interface 150 displays temperature information 508 from the monitoring system 10, including the ambient temperature and the reference tab temperature. The ambient temperature and the reference tab temperature are utilized for calibrating and/or correcting temperature sensed by the first imager 12. Further, the reference tab 132 may be utilized to increase the temperature measurement accuracy of the first imager 12. The caregiver may also monitor the ambient temperature to increase comfort and improve care for the patient within the patient room 56.

Referring still to FIG. 19, the application interface 150 displays patient information 520 from the monitoring system 10 and the support apparatus 80. The patient information 520 generally includes the vital signs information 70 determined by the monitoring system 10, including, for example, the facial temperature, the heart rate, and the respiration rate of the patient. The vital signs information 70 may be at least partially obtained from the thermal image frame 190 and the grayscale image frame 210 displayed on the application interface 150. Additionally or alternatively, the vital signs information 70 may be obtained from multiple image frames 190, 210 that collectively form the first and second image data 14, 22. In such examples, additional thermal and grayscale image frames 190, 210 may be viewed on the application interface 150.

The patient information 520 also includes head coordinates 522 that correspond to the center point 198 in the thermal image frame 190 and the central point 214 in the grayscale image frame 210. The head coordinates 522 may be monitored by the caregiver and/or the monitoring system 10 to detect the movement of the patient. A change in the head coordinates 522 over a predefined threshold (in one or both of the x-direction and the y-direction) may trigger the monitoring system 10 to obtain new image data 14, 22. The monitoring system 10 may obtain new image data 14, 22 and re-optimize the image quality and again determine vital signs information 70 from the patient when the head coordinates 522 change.

Additionally, the patient information 520 includes position information 524 related to a position of the patient on the support apparatus 80. As previously stated, the support apparatus 80 includes position sensors 458 to sense the position of the upper frame 84 as well as weight sensors 460 to sense the position of the patient and the upper frame 84. The information from the sensor assembly 456 of the support apparatus 80 may be utilized to determine the position of the patient on the support apparatus 80 (e.g., supine, side, etc.). The control unit 446 of the support apparatus 80 may calculate the position of the patient and communicate the position information 524 to the caregiver via the communication network 178. The position of the patient may affect the vital signs information 70 detected by the monitoring system 10.

Referring still to FIG. 19, the application interface 150 also includes an interactive actions section 530 that the caregiver may utilize to take certain steps in response to the information displayed on the application interface 150. For example, a log feature 532 may allow the caregiver to store the information from and/or an image or screenshot of the application interface 150 into the electronic medical records 436 stored within the remote server 432. Other actions may be customizable or personalized based on the medical facility 50, the monitoring system 10, or other factors.

Referring to FIGS. 20-25, the remote device 434 may include an application or software for displaying the application interface 150 and providing communication between multiple remote devices 434. The information system 430 allows different caregivers associated with the patient to convey or share information that may not be more formally stored within the electronic medical records 436. A communication aspect of the information system 430 generally provides more convenient and efficient communication between the caregivers associated with the patient.

Figures 20, 21:
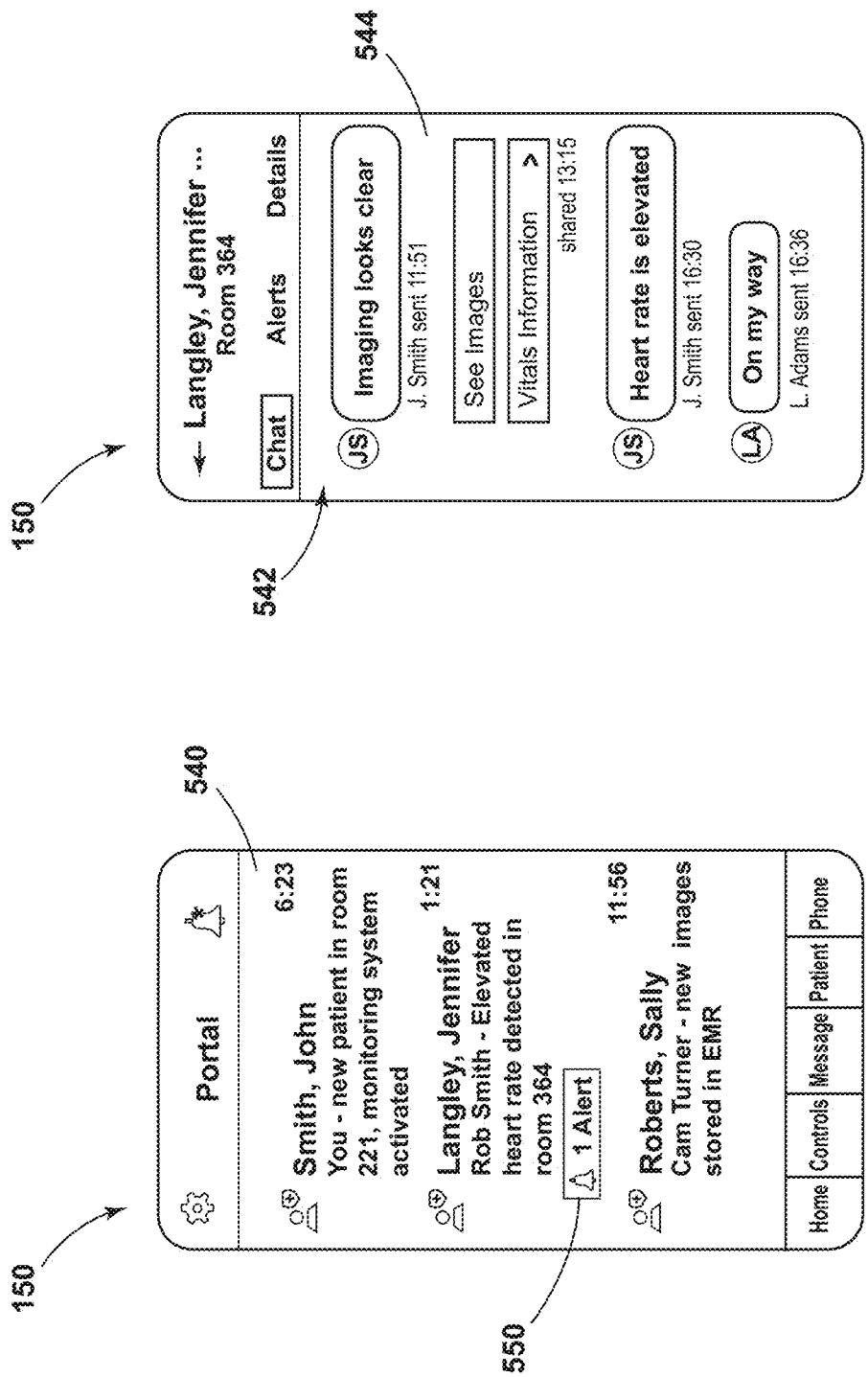
FIG. 20 is representative of an application interface displaying a communication portal, according to the present disclosure.
FIG. 21 is representative of an application interface displaying a chat feature in a patient profile, according to the present disclosure.

As illustrated in FIG. 20, the application interface 150 is configured to display a communication portal 540 for each caregiver, which includes multiple patient profiles 542 that can be accessed through the communication portal 540. Each patient profile 542 corresponds to one patient associated with the caregiver. Each caregiver associated with the patient is granted access to the respective patient profiles 542. Additionally or alternatively, the communication portal 540 provides a way for each caregiver associated with the patient to communicate with one another, as well as a way to receive and communicate updates about the patient.

Referring to FIG. 21, an exemplary patient profile 542 is illustrated on the application interface 150. The patient profile 542 allows for messaging and sharing information (e.g., a chat feature 544) related to the patient between various caregivers throughout the treatment process of the patient at the medical facility 50. The caregivers may directly message one another through the patient profile 542 while the patient is at the medical facility 50. This communication may be stored within the remote device 434 and may be stored within the electronic medical record 436. Alternatively, the communication portal 540 may provide for sharing information that may not be stored in the electronic medical record 436 of the patient. The chat feature 544 may also provide a way for sharing the information from the monitoring system 10 between different caregivers.

Figure 23:
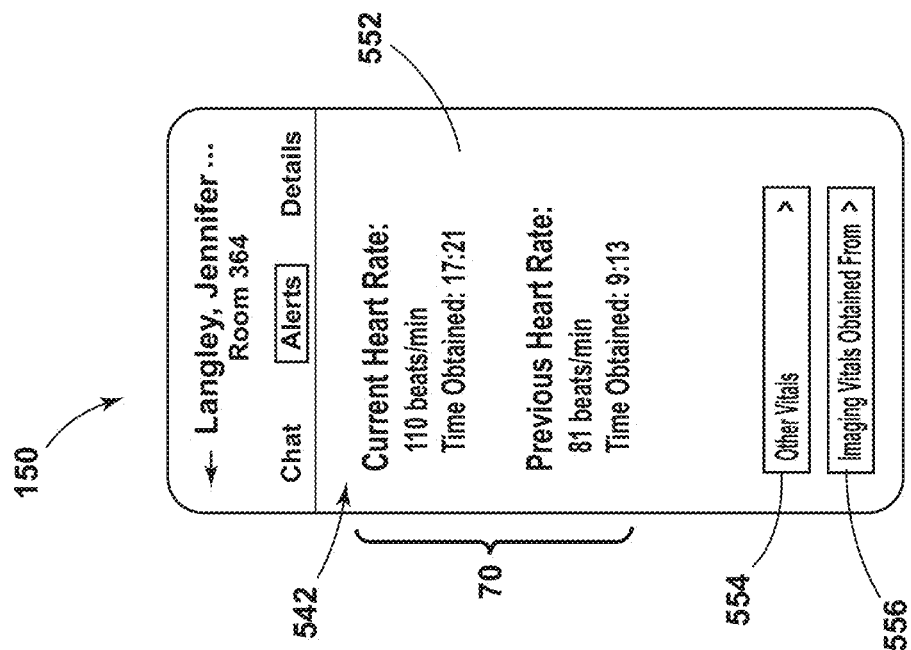
FIG. 23 is representative of an application interface displaying an alert view, according to the present disclosure.
Figure 22:
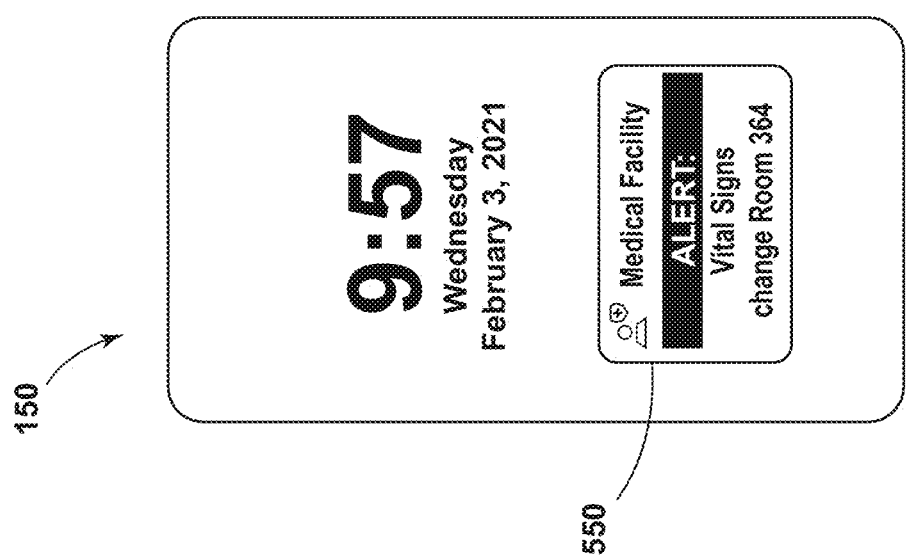
FIG. 22 is representative of an application interface displaying an alert notification, according to the present disclosure.

Referring again to FIG. 20, as well as to FIGS. 22 and 23, the controller 30 of the monitoring system 10 may generate an alert feature 550, which may be viewed through the communication portal 540, as illustrated in FIG. 20, or as a push notification, as illustrated in FIG. 22. The monitoring system 10 may provide the visual alert feature 550 on the application interface 150 through the communication portal 540, the patient profile 542, a locked screen of the remote device 434, etc. The push notification may be advantageous for alerting the caregiver when the application interface 150 is not actively being displayed on the communication portal 540. Additionally or alternatively, the monitoring system 10 may provide an audible or tactile alert feature 550 on the remote device 434 or the facility connected device 422, such as through the nurse call station.

The caregiver may select the visual alert feature 550 on the communication portal 540, causing the application interface 150 to subsequently display an alert view 552 in the patient profile 542, as illustrated in FIG. 23. In the illustrated example, the application interface 150 displays a current detected heart rate determined by the monitoring system 10 and a previous heart rate. The previous heart rate may have been previously obtained from the monitoring system 10 or may have been retrieved from the electronic medical record 436, including a baseline measurement or any previous measurement.

The monitoring system 10 may compare the currently detected vital signs information 70 with previously detected and/or stored vital signs information 70 to generate the alert feature 550. The alert feature 550 may be generated when the vital signs information 70 exceeds a threshold or a threshold range, or when a change in the vital signs information 70 exceeds a threshold or a threshold range. When the application interface 150 is displaying the alert view 552, the application interface 150 may also display selectable features 554, 556 to display other vital signs information 70 and the imaging from which the vital signs information 70 was obtained, respectively.

Figure 24:
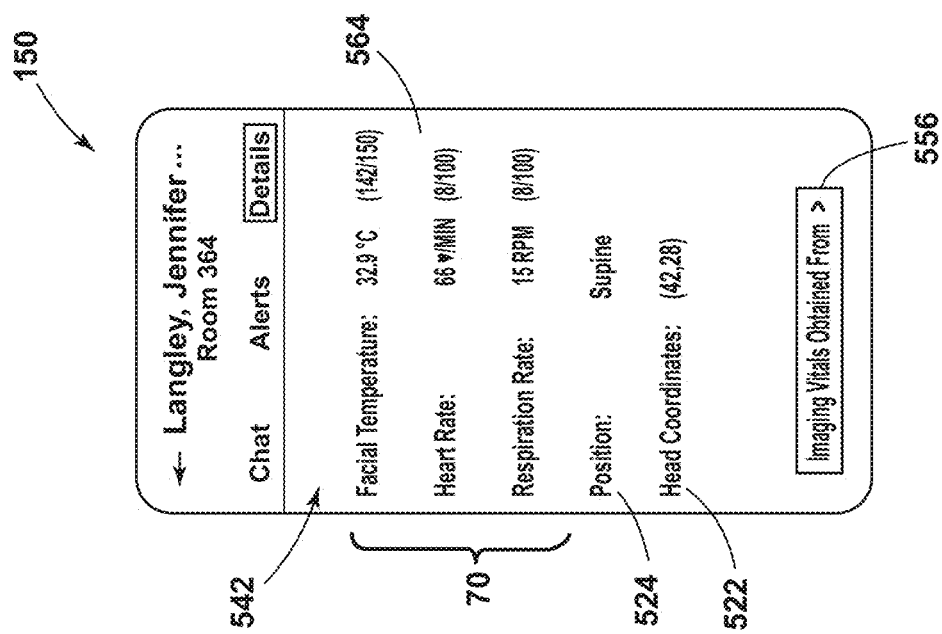
FIG. 24 is representative of an application interface displaying patient information, according to the present disclosure.

Referring to FIG. 24, the application interface 150 may include a details view 564 related to the patient. On the details view 564, the application interface 150 generally displays the patient information 520, including the vital signs information 70, the position of the patient on the support apparatus 80, and the head coordinates 522. The details view 564 may be customizable for the patient to allow the caregiver to view current information relevant to treatment or care in a single location.

Figure 25:
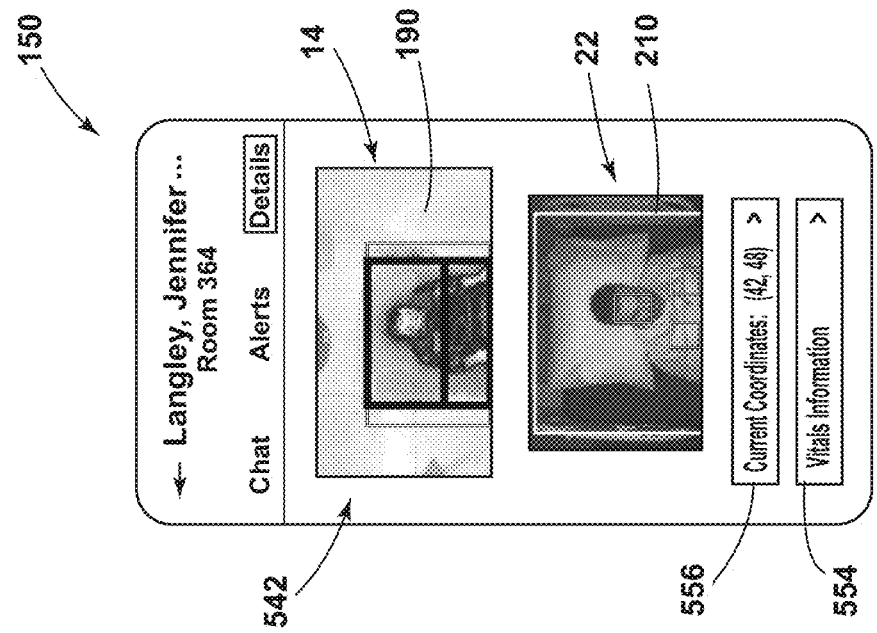
FIG. 25 is representative of an application interface displaying image data obtained by a monitoring system, according to the present disclosure.

Referring to FIG. 25, the application interface 150 displays the first and second image data 14, 22 for viewing by the caregiver. The caregiver may then view the quality of the image, as well as verify the ROIs 34, 216, 218 within the second image data 22 that are utilized to determine the vital signs information 70. The caregiver may also compare the displayed imaging to the current head coordinates 522 displayed on the application interface 150. Viewing the first and second image data 14, 22 may be advantageous for the caregiver to confirm or verify the functions of the monitoring system 10.

Referring still to FIGS. 20-25, the communication aspect of the information system 430 provides a convenient and efficient way for the caregiver to view the information obtained by the monitoring system 10. Depending on the configuration of the application interface 150, the caregiver may view the information simultaneously or on subsequently displayed images. The caregiver may also activate and deactivate the monitoring system 10 from the application interface 150. Moreover, the caregiver may be alerted by the monitoring system 10. Further, the caregivers may convey information from the monitoring system 10 between different caregivers through the information system 430. The monitoring system 10, in conjunction with the information system 430, provides a method for contactless monitoring of the patient and subsequent communication between the caregivers to monitor the information obtained by the monitoring system 10.

Referring to FIGS. 1-25, the monitoring system 10 provides a contactless method for monitoring health information of the patient associated with the monitoring system 10. The monitoring system 10 may be activated through the application interface 150 via the remote device 434 or the facility connected device 422 or through a power feature on the monitor assembly 110. Upon activation, the monitoring system 10 may obtain baseline vital signs information 70. Alternatively, the baseline vital signs information 70 may be obtained by the caregiver using other practicable methods. Once activated, the monitoring system 10 continuously monitors the patient until deactivated by the caregiver.

The monitoring system 10 may be utilized to monitor the movement of the patient. Each instance of the head coordinates 522 being adjusted by the predefined number of pixels may be recorded in the electronic medical record 436 and/or communicated to the caregiver via the patient profile 542. Further, through the object recognition routine 174, the monitoring system 10 may determine that the patient is not disposed on the support apparatus 80. If the monitoring system 10 is activated and the patient is not on the support apparatus 80, the monitoring system 10 may issue an alert to the caregiver that the patient has left the support apparatus 80.

Further, the monitoring system 10 is utilized for monitoring the vital signs information 70 of the patient. The monitoring system 10 captures the first image data 14 and the second image data 22, which are each communicated to the controller 30. The first image data 14 is utilized to determine the facial region 32 and the center point 198 of the facial region 32. The center point 198 is mapped onto the second image data 22, such that each center point 198 has the same coordinate within the operating boundaries 192, 212 on the first and second image data 14, 22, respectively. Utilizing the center point 198 on the first and the second image data 22, the facial ROI 34 is determined by the controller 30. The chest ROIs 216, 218 are also determined utilizing the facial ROI 34 and the central point 214. The facial region 32 and the facial and chest regions of interest 34, 216, 218 are utilized to determine vital signs information 70 of the patient being monitored, including, but not limited to, heart rate, respiration rate, and facial temperature.

The monitoring system 10 includes at least one routine 174 for optimizing the image quality of the second image data 22. Optimizing the image quality of the second image data 22 increases pixel value contrast within the second image data 22, and consequently improves the accuracy of the vital signs information 70 and allows the caregiver to provide improved care based on the improved accuracy. The monitoring system 10 automatically optimizes the image quality of the second image data 22 based on the average pixel value, $P_{avg}$, in the facial ROI 34 of the second image data 22.

The monitoring system 10 may optimize the image quality in a variety of ways. For example, the monitoring system 10 may adjust the intensity of the NIR light 28 emitted by the emitter 26 by sending the pulse width modulation signal to the light control circuitry 182. The change in intensity may improve pixel contrast of the pixels 220 within the facial ROI 34. Additionally or alternatively, the monitoring system 10 may adjust the exposure of the second imager 20 to improve the contrast of the pixels 220 within the facial ROI 34. The monitoring system 10 may increase or decrease the shutter speed for capturing the second image data 22, which consequently adjust the exposure of the second imager 20.

Further, the monitoring system 10 may adjust both the intensity of the light 28 emitted by the emitter 26 and the exposure of the second imager 20. The controller 30 utilizes the average pixel value, $P_{avg}$, of the facial ROI 34 and the exposure to determine whether the intensity of the light 28 and/or the exposure should be adjusted. The controller 30 may store information to determine which method (e.g., adjusting intensity, adjusting exposure, or adjusting both) is utilized to optimize the image quality. For example, adjusting exposure rather than intensity may prolong the use of the light source 160. Additionally or alternatively, the caregiver may choose which routine 174 is utilized by the monitoring system 10. Through optimizing the image quality of the second image data 22, the vital signs information 70 may be more accurate, allowing for improved monitoring of the patient.

Use of the present system may provide for a variety of advantages. For example, the monitoring system 10 may utilize the first imager 12 to obtain thermal image data and the second imager 20 to obtain monochromatic or grayscale image data. Additionally, the monitoring system 10 may utilize the first image data 14 to determine the facial ROI 34 on the second image data 22. Further, the monitoring system 10 may use the facial ROI 34 to optimize the image quality of second image data 22. Also, the monitoring system 10 may calculate the average pixel value, $P_{avg}$, within the facial ROI 34 and, in response to the average pixel value, $P_{avg}$, may adjust at least one of the emitter 26 and the second imager 20 of the monitoring system 10 to optimize image quality. Further, the monitoring system 10 may adjust the intensity of light 28 emitted by the emitter 26, the exposure of the second imager 20, or a combination thereof. Additionally, the monitoring system 10 may utilize at least one of the first image data 14 and the second image data 22 to obtain vital signs information 70 of the patient in a contactless manner.

Further, the monitoring system 10 may be in communication with the remote server 432 and the support apparatus 80 to obtain additional information about the patient that may affect the vital signs information 70. Moreover, the monitoring system 10 may communicate with the remote server 432 and the support apparatus 80 and subsequently generate an alert communicated via the application interface 150. Also, the support apparatus 80 may detect the position of the patient on the support apparatus 80. Additionally, the monitoring system 10 may be associated with the information system 430 of the medical facility 50. Also, the information system 430 provides the application interface 150 that may be displayed via the remote device 434 and/or the facility connected device 422 to display the vital signs information 70, the patient information 520, the alert feature 550, and other information to the caregiver. Moreover, the information from the monitoring system 10 may be stored within the electronic medical record 436 for the respective patient and may be communicated between caregivers via the communication portal 540. Additional benefits and advantages may be realized and/or achieved.

The device disclosed herein is further summarized in the following paragraphs and is further characterized by combinations of any and all of the various aspects described therein.

According to another aspect of the present disclosure, a contactless patient monitoring system includes a first imager configured to capture first image data of a target area within a first field of view. A second imager is operably coupled to the first imager. The second imager is configured to capture second image data of the target area within a second field of view. An emitter is operably coupled to at least one of the first imager and the second imager. The emitter is configured to emit light within a predetermined wavelength range. A controller is communicatively coupled to the first imager, the second imager, and the emitter. The controller is configured to determine a facial region of a person in the first image data, determine a region of interest in the second image data that coincides with the facial region in the first image data, calculate a pixel value within the region of interest, adjust at least one of the emitter and the second imager when the pixel value is outside a predetermined pixel value range, and determine vital signs information from at least one of the first image data and the second image data.

According to another aspect of the present disclosure, a controller is configured to adjust an exposure of a second imager in response to a pixel value.

According to another aspect of the present disclosure, a second imager has a maximum allowable exposure based on a frame rate. A controller is configured to compare an exposure of the second imager with the maximum allowable exposure in response to a pixel value.

According to another aspect of the present disclosure, a controller is configured to adjust an exposure of a second imager if the exposure is less than a maximum allowable exposure. The controller is configured to adjust an intensity of light emitted by an emitter if the exposure of the second imager is at least equal to the maximum allowable exposure.

According to another aspect of the present disclosure, a controller is configured to adjust an intensity of light emitted from an emitter in response to a pixel value.

According to another aspect of the present disclosure, vital signs information includes at least one of a facial temperature, a heart rate, and a respiration rate.

According to another aspect of the present disclosure, a controller is configured to generate an alert when vital signs information is outside a predefined range.

According to another aspect of the present disclosure, a support apparatus is in communication with a controller. A target area includes at least a portion of the support apparatus. The support apparatus includes a sensor assembly for sensing at least one of a position of the support apparatus and a position of a person on the support apparatus.

According to another aspect of the present disclosure, second image data includes a plurality of pixels within a region of interest. Each pixel has a local pixel value. A pixel value calculated by a controller is an average pixel value determined by the following equation: $P_{avg}=1/n \cdot \Sigma_{k=1}^{n} P_k$, where Pang is the average pixel value, $P_k$ is the local pixel value in the region of interest, and n is a total number of pixels within the region of interest.

According to another aspect of the present disclosure, a predetermined wavelength range is from 800 nm to 900 nm. A first imager is a thermal imager and first image data thermal image data. A second imager is a monochromatic imager and second image data is monochromatic image data. The vital signs information includes a facial temperature, a heart rate, and a respiration rate According to another aspect of the present disclosure, a patient monitoring system includes a first imager configured to capture first image data within a first field of view. A second imager is configured to capture second image data within a second field of view. A controller is communicatively coupled to the first imager and the second imager. The controller is configured to determine a facial region in the first image data, determine a region of interest within the second image data that coincides with the facial region in the first image data, calculate a pixel value within the region of interest, and adjust an exposure of the second imager in response to the second image data.

According to another aspect of the present disclosure, second image data includes multiple image frames captured by a second imager. A maximum allowable exposure is a time between consecutive image frames being communicated to a controller.

According to another aspect of the present disclosure, a controller is configured to calculate a pixel value of regions of interest in each image frame.

According to another aspect of the present disclosure, a controller is configured to adjust an exposure to between 15 ms and 30 ms when a pixel value is outside a predetermined pixel value range.

According to another aspect of the present disclosure, a target area is within a first field of view and a second field of view. A controller is configured to determine vital signs information of a person within the target area.

According to another aspect of the present disclosure, a controller is configured to communicate vital signs information to at least one of a server storing electronic medical records and a remote device having patient information.

According to another aspect of the present disclosure, a controller is configured to analyze pixels of second image data to determine vital signs information.

According to another aspect of the present disclosure, an emitter is communicatively coupled to a controller and is configured to emit near infrared light having a wavelength in a range from 800 nm to 900 nm. An emitter is configured to emit near infrared light into a second field of view of a second imager.

According to another aspect of the present disclosure, a first imager is a thermal camera configured to operate within a long wavelength infrared spectrum having a wavelength range from 8 µm to 14 µm.

According to another aspect of the present disclosure, a second imager is a monochromatic camera configured to operate in a near infrared spectrum having a wavelength range from 800 nm to 900 nm.

According to another aspect of the present disclosure, a pixel value calculated by the controller is an average pixel value within a region of interest.

According to another aspect of the present disclosure, a monitoring system for a medical facility includes a thermal imager configured to capture thermal image data. A monochromatic imager is configured to capture monochromatic image data. An emitter has a light source operably coupled to light control circuitry. A controller is communicatively coupled to the thermal imager, the monochromatic imager, and the emitter. The controller is configured to determine a thermal facial region within the thermal image data, map a region of interest onto the monochromatic image data that coincides with the thermal facial region, calculate a pixel value within the region of interest in the monochromatic image data, and adjust an intensity of light emitted by the light source in response to the pixel value.

According to another aspect of the present disclosure, an intensity of the light is adjusted via pulse width modulation.

According to another aspect of the present disclosure, a controller is configured to compare a pixel value with a predetermined pixel value range stored in the controller.

According to another aspect of the present disclosure, a controller is configured to determine coordinates of a center point of thermal facial region within the thermal image data. The controller is configured to map a corresponding central point on monochromatic image data utilizing the coordinates.

According to another aspect of the present disclosure, a light source is a light-emitting diode configured to emit light in a near infrared spectrum having a wavelength in a range from 800 nm to 900 nm.

According to another aspect of the present disclosure, a monochromatic imager includes a bandwidth filter configured to allow near infrared light having a wavelength range from 800 nm to 900 nm.

According to another aspect of the present disclosure, a thermal facial region is a thermal facial contour within thermal image data.

According to another aspect of the present disclosure, a monochromatic image data is configured as grayscale image data.

According to another aspect of the present disclosure, a pixel value calculated by the controller is an average pixel value. Vital signs information includes a facial temperature, a heart rate, and a respiration rate.

According to another aspect of the present disclosure, a controller is configured to adjust an exposure of a second imager to between 15 ms and 30 ms in response to a pixel value.

According to another aspect of the present disclosure, a contactless patient monitoring system includes a first imager is configured to capture first image data. A second imager is configured to capture second image data. An emitter is disposed proximate to at least the second imager. The emitter is configured to emit light. A controller is configured to communicate with the first imager, the second imager, and the emitter. The controller is configured to determine a center point of a facial region utilizing a first image data received from the first imager, map a corresponding central point on a second image data received from the second imager that coincides with the center point of the facial region of the first image data, determine a region of interest on the second image data utilizing the central point, calculate a pixel value within the region of interest, compare the pixel value with a predetermined pixel value range, and adjust at least one of an exposure of the second imager and an intensity of light emitted by the emitter if the pixel value is outside of the predetermined pixel value range.

According to another aspect of the present disclosure, a controller is configured to adjust an exposure of a monochromatic imager to between 15 ms and 30 ms.

According to another aspect of the present disclosure, a controller is configured to adjust an intensity of light emitted by an emitter via pulse width modulation.

According to another aspect of the present disclosure, a region of interest is a facial region of interest. A controller is configured to determine a chest region of interest utilizing a central point within a facial region of interest.

According to another aspect of the present disclosure, a controller is configured to determine vital signs information of a patient utilizing a facial region of interest and a chest region of interest.

According to another aspect of the present disclosure, a controller is configured to communicate vital signs information to be displayed on an application interface. The vital signs information includes at least one of a facial temperature, a heart rate, and a respiration rate.

According to another aspect of the present disclosure, a controller is configured to communicate with a support apparatus. The support apparatus is configured to determine position information of a person on the support apparatus and communicate the position information to the controller.

According to another aspect of the present disclosure, a pixel value calculated by the controller is an average pixel value. Second image data includes a plurality of pixels within a region of interest. Each pixel has a local pixel value. The average pixel value is determined based on the local pixel value for each pixel of the plurality of pixels and a total number of pixels within the region of interest.

According to another aspect of the present disclosure, second image data includes a plurality of pixels within a region of interest. Each pixel has a local pixel value. An average pixel value is determined with the following equation:

$$P_{avg} = \frac{1}{n} \cdot \sum_{k=1}^{n} P_k,$$

where $P_{avg}$ is the average pixel value, $P_k$ is the local pixel value in the region of interest, and n is a total number of pixels within the region of interest.

According to another aspect of the present disclosure, a method of optimizing image quality in a patient monitoring system includes: capturing a first image with a first imager; determining a contour corresponding to a facial region of a patient within the first image; capturing a second image with a second imager; mapping a facial region of interest on the second image that corresponds with the facial region of the first image; calculating a pixel value within the facial region of interest; comparing the pixel value with a predetermined pixel value range; and adjusting at least one of the second imager and an emitter if the pixel value is outside of the predetermined pixel value range.

According to another aspect of the present disclosure, near infrared light is emitted from an emitter into a field of view of a second imager.

According to another aspect of the present disclosure, a step of adjusting at least one of a second imager and an emitter includes adjusting an intensity of light emitted by an emitter.

According to another aspect of the present disclosure, a step of adjusting at least one of a second imager and an emitter includes determining a maximum allowable exposure of the second imager based on a frame rate of the second imager and comparing an exposure of the second imager with the maximum allowable exposure.

According to another aspect of the present disclosure, a step of adjusting at least one of a second imager and an emitter includes adjusting an exposure of the second imager if the exposure is less than a maximum allowable exposure.

According to another aspect of the present disclosure, a step of adjusting at least one of a second imager and a emitter includes adjusting an intensity of light emitted by the emitter if an exposure is at least equal to a maximum allowable exposure.

According to another aspect of the present disclosure, a step of calculating a pixel value within a facial region of interest includes calculating an average pixel value within the facial region of interest.

According to another aspect of the present disclosure, a monitoring system for a medical facility includes a controller configured to communicate with a first imager, a second imager, and an emitter. The controller is configured to determine a facial region within first image data captured by the first imager, determine a facial region of interest on second image data captured by the second imager utilizing the facial region, calculate a pixel value within the facial region of interest, and adjust at least one of the emitter and the second imager in response to the pixel value.

According to another aspect of the present disclosure, a controller is configured to determine vital signs information from second image data.

According to another aspect of the present disclosure, a controller is configured to analyze pixel values of pixels within second image data to determine vital signs information.

According to another aspect of the present disclosure, a controller is configured to communicate vital signs information for display on an application interface.

According to another aspect of the present disclosure, a controller is configured to adjust an intensity of near infrared light emitted from an emitter if a pixel value is outside a predetermined pixel value range.

According to another aspect of the present disclosure, a controller is configured to adjust an exposure of a second imager if a pixel value is outside a predetermined pixel value range.

According to another aspect of the present disclosure, a controller is configured to communicate first image data and second image data for display on an application interface.

According to another aspect of the present disclosure, a controller is configured to communicate with a remote server that has electronic medical records. The controller is configured to compare vital signs information determined by the controller with previous vital signs information stored in an electronic medical record.

According to another aspect of the present disclosure, a controller is configured to generate an alert communicated via an application interface if at least one of vital signs information exceeds a predefined range and a change in the vital signs information exceeds a predefined change range.

According to another aspect of the present disclosure, a controller is configured to communicate with a support apparatus. The support apparatus is configured to determine a position of a patient on the support apparatus.

According to another aspect of the present disclosure, a controller is configured to determine a maximum allowable exposure of a second imager based on a frame rate.

According to another aspect of the present disclosure, a controller is configured to adjust an exposure of a second imager if the exposure is less than a maximum allowable exposure. The controller is configured to adjust an intensity of light emitted by an emitter if the exposure is at least equal to the maximum allowable exposure.

According to another aspect of the present disclosure, a pixel value calculated by the controller is an average pixel value within a facial region of interest.

According to another aspect, a contactless patient monitoring system includes a means for capturing first image data of a target area within a first field of view and a means for capturing second image data of the target area within a second field of view. A means for emitting light is operably coupled to the at least one of the means for capturing first image data and the means for capturing second image data. The means for emitting light is configured to emit light within a predetermined wavelength range. A means for processing is communicatively coupled to the means for capturing first image data, the means for capturing second image data, and the means for emitting light. The means for processing is configured to determine a facial region of a person in the first image data, determine a region of interest in the second image data that coincides with the facial region in the first image data, and calculate a pixel value within the region of interest.

Related applications, for example those listed herein, are fully incorporated by reference. Descriptions within the related applications are intended to contribute to the description of the information disclosed herein as may be relied upon by a person of ordinary skill in the art. Any changes between any of the related applications and the present disclosure are not intended to limit the description of the information disclosed herein, including the claims. Accordingly, the present application includes the description of the information disclosed herein as well as the description of the information in any or all of the related applications.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, are illustrative only. Although only a few embodiments of the present innovations have been described in detail in this disclosure, those skilled in the art who review this disclosure will readily appreciate that many modifications are possible (e.g., variations in sizes, dimensions, structures, shapes, and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A contactless patient monitoring system, comprising:
   a housing;
   a thermal imager coupled to the housing, wherein the thermal imager is sensitive to a longwave infrared spectrum and configured to capture thermal image data of a target area within a first field of view;
   a monochromatic imager operably coupled to the thermal imager and the housing, wherein the monochromatic imager is configured to operate within a near infrared light bandwidth and to capture grayscale image data of the target area within a second field of view;
   an emitter operably coupled to the housing, wherein the emitter is configured to emit light within the near infrared light bandwidth proximate to the housing; and
   a controller communicatively coupled to the thermal imager, the monochromatic imager, and the emitter, wherein the controller is configured to:
      determine a facial region of a person in the thermal image data;
      determine a region of interest in the grayscale image data that coincides with the facial region in the thermal image data;
      calculate a pixel value within the region of interest;
      adjust at least one of the emitter and the monochromatic imager when the pixel value is outside a predetermined pixel value range; and
      determine vital signs information from each of the thermal image data and the grayscale image data.

2. The contactless patient monitoring system claim 1, wherein the controller is configured to adjust an exposure of the monochromatic imager in response to the pixel value.

3. The contactless patient monitoring system of claim 2, wherein the monochromatic imager has a maximum allowable exposure based on a frame rate, and wherein the controller is configured to compare the exposure of the monochromatic imager with the maximum allowable exposure in response to the pixel value.

4. The contactless patient monitoring system of claim 3, wherein the controller is configured to adjust the exposure of the monochromatic imager if the exposure is less than the maximum allowable exposure, and wherein the controller is configured to adjust an intensity of the light emitted by the emitter if the exposure of the monochromatic imager is at least equal to the maximum allowable exposure.

5. The contactless patient monitoring system of claim 1, wherein the controller is configured to adjust an intensity of the light emitted from the emitter in response to the pixel value.

6. The contactless patient monitoring system of claim 1, further comprising:
   a support apparatus in communication with the controller, wherein the target area includes at least a portion of the support apparatus, and wherein the support apparatus includes a sensor assembly for sensing at least one of a position of the support apparatus and a position of the person on the support apparatus.

7. The contactless patient monitoring system of claim 1, wherein the grayscale image data includes a plurality of pixels within the region of interest, wherein each pixel has a local pixel value, and wherein the pixel value calculated by the controller is an average pixel value within the region of interest determined with the following equation:

$$P_{avg} = 1/n \cdot \Sigma_{k=1}^{n} P_k,$$

where $P_{avg}$ is the average pixel value, $P_k$ is the local pixel value in the region of interest, and n is a total number of pixels within the region of interest.

8. The contactless patient monitoring system of claim 1, wherein the light within the near infrared light bandwidth emitted by the emitter has a wavelength in a range of from 800 nm to 900 nm, and wherein the vital signs information includes a facial temperature, a heart rate, and a respiration rate.

9. A monitoring system for a medical facility, comprising:
a thermal imager configured to capture thermal image data;
a monochromatic imager configured to capture monochromatic image data;
an emitter having a light source operably coupled to light control circuitry; and
a controller communicatively coupled to the thermal imager, the monochromatic imager, and the emitter, wherein the controller is configured to:
determine a thermal facial region within the thermal image data;
map a region of interest onto the monochromatic image data that coincides with the thermal facial region;
calculate a pixel value within the region of interest in the monochromatic image data;
compare a calculated pixel value to a predetermined pixel value range;
adjust an intensity of light emitted by the light source when the calculated pixel value is outside of the predetermined pixel value range;
recapture the monochromatic image data with an adjusted intensity of light emitted by the light source; and
determine vital signs information from the monochromatic image data when the calculated pixel value is within the predetermined pixel value range.

10. The monitoring system of any one of claim 9, wherein the controller is configured to determine coordinates of a center point of the thermal facial region within the thermal image data, and wherein the controller is configured to map a corresponding central point on the monochromatic image data utilizing the coordinates.

11. The monitoring system of claim 9, wherein the light source is a light emitting diode configured to emit the light is a near infrared spectrum having a wavelength in a range from 800 nm to 900 nm.

12. The monitoring system of claim 9, wherein the monochromatic imager includes a bandwidth filter configured to allow near infrared light having a wavelength range from 800 nm to 900 nm.

13. The monitoring system of claim 9, wherein the calculated pixel value calculated by the controller is an average pixel value.

14. The monitoring system of claim 9, wherein the controller is configured to adjust an exposure of the monochromatic imager to between 15 ms and 30 ms in response to the pixel value.

15. A contactless patient monitoring system, comprising:
a thermal imager configured to capture thermal image data;
a monochromatic imager configured to capture grayscale image data;
an emitter disposed proximate to at least the monochromatic imager, wherein the emitter is configured to emit light; and
a controller configured to communicate with the thermal imager, the monochromatic imager, and the emitter, wherein the controller is configured to:
determine a center point of a facial region utilizing the thermal image data received from the thermal imager;
map a corresponding central point on the grayscale image data received from the monochromatic imager that coincides with the center point of the facial region of the thermal image data;
determine a region of interest on the grayscale image data utilizing the corresponding central point;
calculate a pixel value within the region of interest;
compare the pixel value with a predetermined pixel value range;
adjust an exposure of the monochromatic imager when a calculated pixel value is outside of the predetermined pixel value range and when the exposure is less than a predetermined maximum exposure value;
adjust an intensity of light emitted by the emitter when the calculated pixel value is outside the predetermined pixel value range and when the exposure is at least equal to the predetermined maximum exposure value; and
determine vital signs information from at least one of the thermal image data and the grayscale image data when the calculated pixel value is within the predetermined pixel value range.

16. The contactless patient monitoring system of claim 15, wherein the controller is configured to adjust the exposure of the monochromatic imager to between 15 ms and 30 ms.

17. The contactless patient monitoring system of claim 15, wherein the controller is configured to adjust the intensity of the light emitted by the emitter via pulse width modulation.

18. The contactless patient monitoring system of claim 15, wherein the region of interest is a facial region of interest, and wherein the controller is configured to determine a chest region of interest utilizing the corresponding central point within the facial region of interest.

19. The contactless patient monitoring system of claim 18, wherein the controller is configured to determine the vital signs information of a patient utilizing the facial region of interest and the chest region of interest.

20. The contactless patient monitoring system of claim 15, wherein the calculated pixel value calculated by the controller is an average pixel value, wherein the grayscale image data includes a plurality of pixels within the region of interest, wherein each pixel has a local pixel value, and wherein the average pixel value is determined based on the local pixel value for each pixel of the plurality of pixels and a total number of pixels within the region of interest.

* * * * *